(12) United States Patent
Kake et al.

(10) Patent No.: US 11,237,647 B2
(45) Date of Patent: Feb. 1, 2022

(54) COORDINATE INPUT PROCESSING APPARATUS, EMOTION ESTIMATION APPARATUS, EMOTION ESTIMATION SYSTEM, AND BUILDING APPARATUS FOR BUILDING EMOTION ESTIMATION-ORIENTED DATABASE

(71) Applicant: Wacom Co., Ltd., Saitama (JP)

(72) Inventors: Akiyuki Kake, Tokyo (JP); Heidi Wang, Krefeld (DE)

(73) Assignee: Wacom Co., Ltd., Saitama (JP)

( * ) Notice: Subject to any disclaimer, the term of this patent is extended or adjusted under 35 U.S.C. 154(b) by 0 days.

(21) Appl. No.: 16/284,867

(22) Filed: Feb. 25, 2019

(65) Prior Publication Data
US 2019/0187823 A1    Jun. 20, 2019

Related U.S. Application Data

(63) Continuation of application No. PCT/JP2017/028676, filed on Aug. 8, 2017.

(30) Foreign Application Priority Data

Sep. 1, 2016 (JP) .............................. JP2016-170574
Dec. 22, 2016 (JP) .............................. JP2016-249336

(51) Int. Cl.
*G06F 3/0354* (2013.01)
*G06F 3/01* (2006.01)
(Continued)

(52) U.S. Cl.
CPC ........ *G06F 3/03545* (2013.01); *A61B 5/0022* (2013.01); *A61B 5/16* (2013.01);
(Continued)

(58) Field of Classification Search
CPC . G06F 3/01; G06F 3/011; G06F 3/015; G06F 3/03; G06F 3/03545; G06F 3/038;
(Continued)

(56) References Cited

U.S. PATENT DOCUMENTS 6,855,112 B2 * 2/2005 Kao .................... A61B 5/0482
                                                   600/300
2005/0114142 A1 * 5/2005 Asukai ..................... A61B 5/16
                                                   704/270
(Continued)

FOREIGN PATENT DOCUMENTS

CN      103926997 A      7/2014
GB      2 413 425 A      10/2005
(Continued)

OTHER PUBLICATIONS

Extended European Search Report, dated Jul. 18, 2019, for European Application No. 17846070.5, 10 pages.

*Primary Examiner* — Jason M Mandeville
(74) *Attorney, Agent, or Firm* — Seed IP Law Group LLP

(57) ABSTRACT

A position detection apparatus includes a sensor that detects a position pointed to by an electronic pen and circuitry that acquires pen state information regarding the electronic pen held by a person; a transmitter that transmits to an emotion estimation apparatus an emotional state estimation request including the acquired pen state information, the emotion estimation apparatus including a database that stores information regarding an emotional state of the person holding the electronic pen and range information regarding a range of values that may be taken by the pen state information regarding the electronic pen, the emotional state and the range information being associated with one another; and a processor that receives information corresponding to the emotional state transmitted from the emotion estimation apparatus in response to the pen state information included
(Continued)

in the transmitted emotional state estimation request, and performs processing using the received information corresponding to the emotional state.

26 Claims, 19 Drawing Sheets

(51) Int. Cl.

| | | |
|---|---|---|
| *G06F 3/03* | (2006.01) | |
| *A61B 5/16* | (2006.01) | |
| *G06F 3/041* | (2006.01) | |
| *G06F 3/0488* | (2013.01) | |
| *G06K 9/62* | (2006.01) | |
| *G06K 9/00* | (2006.01) | |
| *G06F 3/046* | (2006.01) | |
| *A61B 5/00* | (2006.01) | |
| *G06K 9/22* | (2006.01) | |
| *G06F 3/038* | (2013.01) | |
| *A61B 5/11* | (2006.01) | |

(52) U.S. Cl.
CPC ............ *A61B 5/165* (2013.01); *A61B 5/6814* (2013.01); *A61B 5/6898* (2013.01); *A61B 5/7267* (2013.01); *G06F 3/01* (2013.01); *G06F 3/011* (2013.01); *G06F 3/015* (2013.01); *G06F 3/03* (2013.01); *G06F 3/038* (2013.01); *G06F 3/041* (2013.01); *G06F 3/046* (2013.01); *G06F 3/0488* (2013.01); *G06K 9/00167* (2013.01); *G06K 9/00422* (2013.01); *G06K 9/00536* (2013.01); *G06K 9/222* (2013.01); *G06K 9/6217* (2013.01); *A61B 5/1114* (2013.01); *A61B 5/7246* (2013.01); *G06F 2203/011* (2013.01)

(58) Field of Classification Search
CPC ........ G06F 3/046; G06F 3/0488; G06F 3/041; G06F 2203/011; G06K 9/00422; G06K 9/00536; G06K 9/00167; G06K 9/222; G06K 9/6217; A61B 5/0022; A61B 5/0476; A61B 5/1114; A61B 5/16; A61B 5/7267; A61B 5/165; A61B 5/7246; A61B 5/6898; A61B 5/6814
USPC ......................................................... 345/179
See application file for complete search history.

(56) References Cited

U.S. PATENT DOCUMENTS

| | | | |
|---|---|---|---|
| 2009/0264713 A1 | 10/2009 | Van Loenen et al. | |
| 2015/0347003 A1* | 12/2015 | Oh ................. | G06F 40/109 |
| | | | 382/119 |
| 2017/0192534 A1* | 7/2017 | Han ................. | G06F 3/0383 |

FOREIGN PATENT DOCUMENTS

| | | | | |
|---|---|---|---|---|
| GB | 2413425 A | * | 10/2005 | ............ G06K 9/222 |
| JP | 2005-065252 A | | 3/2005 | |
| JP | 2010-131328 A | | 6/2010 | |
| JP | 2014-139759 A | | 7/2014 | |
| JP | 2015-102886 A | | 6/2015 | |
| JP | 2015-109964 A | | 6/2015 | |

* cited by examiner

FIG.5
| | |
|---|---|
| RELAXED STATE | 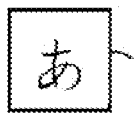 FL |
| CONCENTRATED STATE | 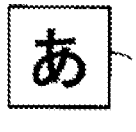 FL |
| IRRITATED STATE |  FL |
| DISTRACTED STATE | 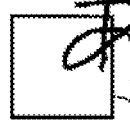 FL |
| ANGRY STATE | 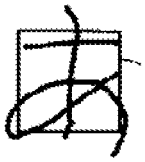 FL |

FIG. 6

EMOTION ESTIMATION-ORIENTED DATABASE

| PEN ID | EMOTIONAL STATE | COORDINATE POSITION BLUR | WRITING PRESSURE | TILT | HEIGHT POSITION | HOVERING POSITION BLUR |
|---|---|---|---|---|---|---|
| ID1 | RELAXED |  | Pra1~Prb1 | SLa1~SLb1 | Ha1~Hb1 | Ara1~Arb1 |
| | CONCENTRATED |  | Pra2~Prb2 | SLa2~SLb2 | Ha2~Hb2 | Ara2~Arb2 |
| | IRRITATED |  | Pra3~Prb3 | SLa3~SLb3 | Ha3~Hb3 | Ara3~Arb3 |
| | DISTRACTED |  | Pra4~Prb4 | SLa4~SLb4 | Ha4~Hb4 | Ara4~Arb4 |
| | ANGRY |  | Pra5~Prb5 | SLa5~SLb5 | Ha5~Hb5 | Ara5~Arb5 |
| ID2 | | | | | | |

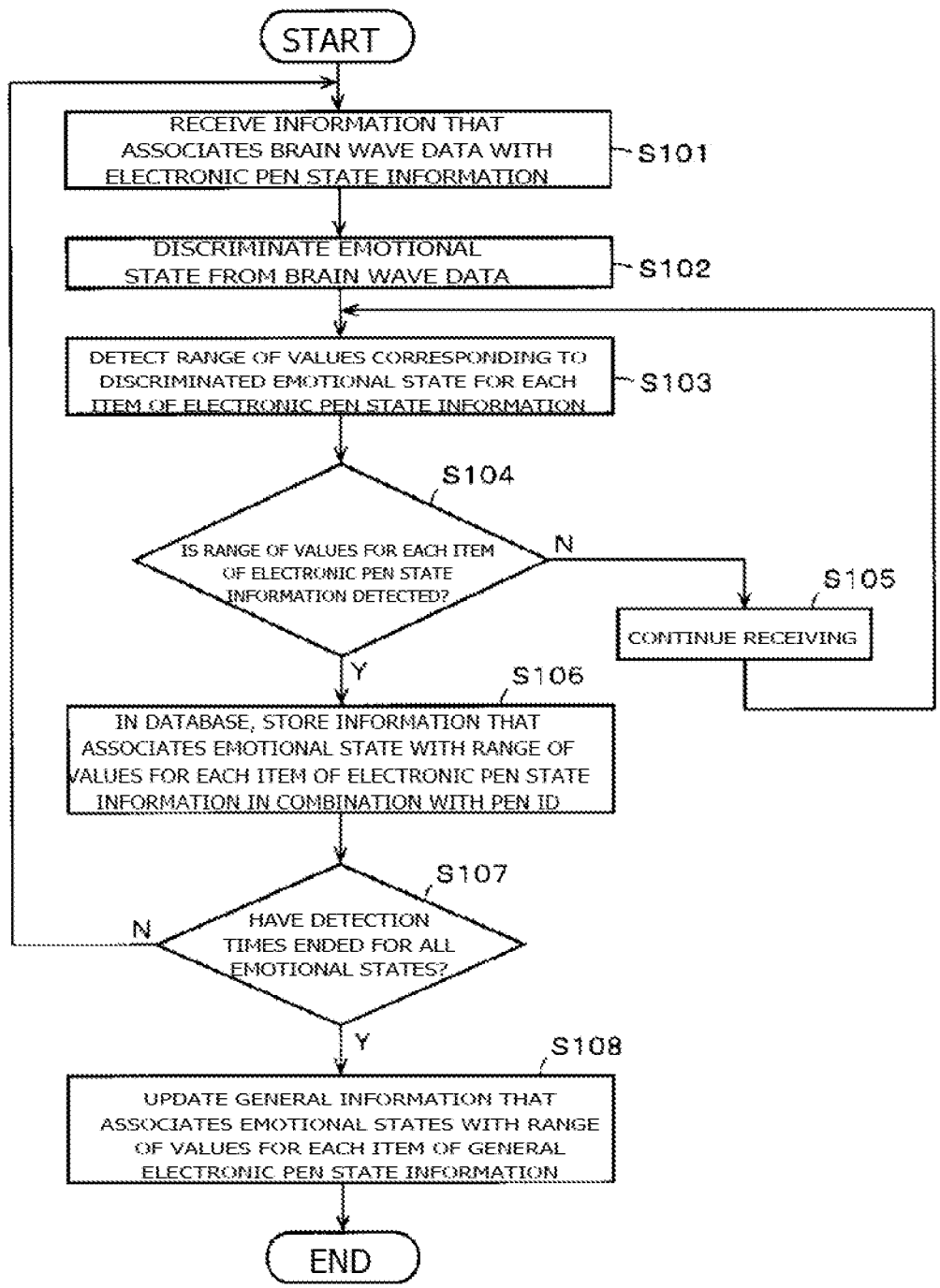

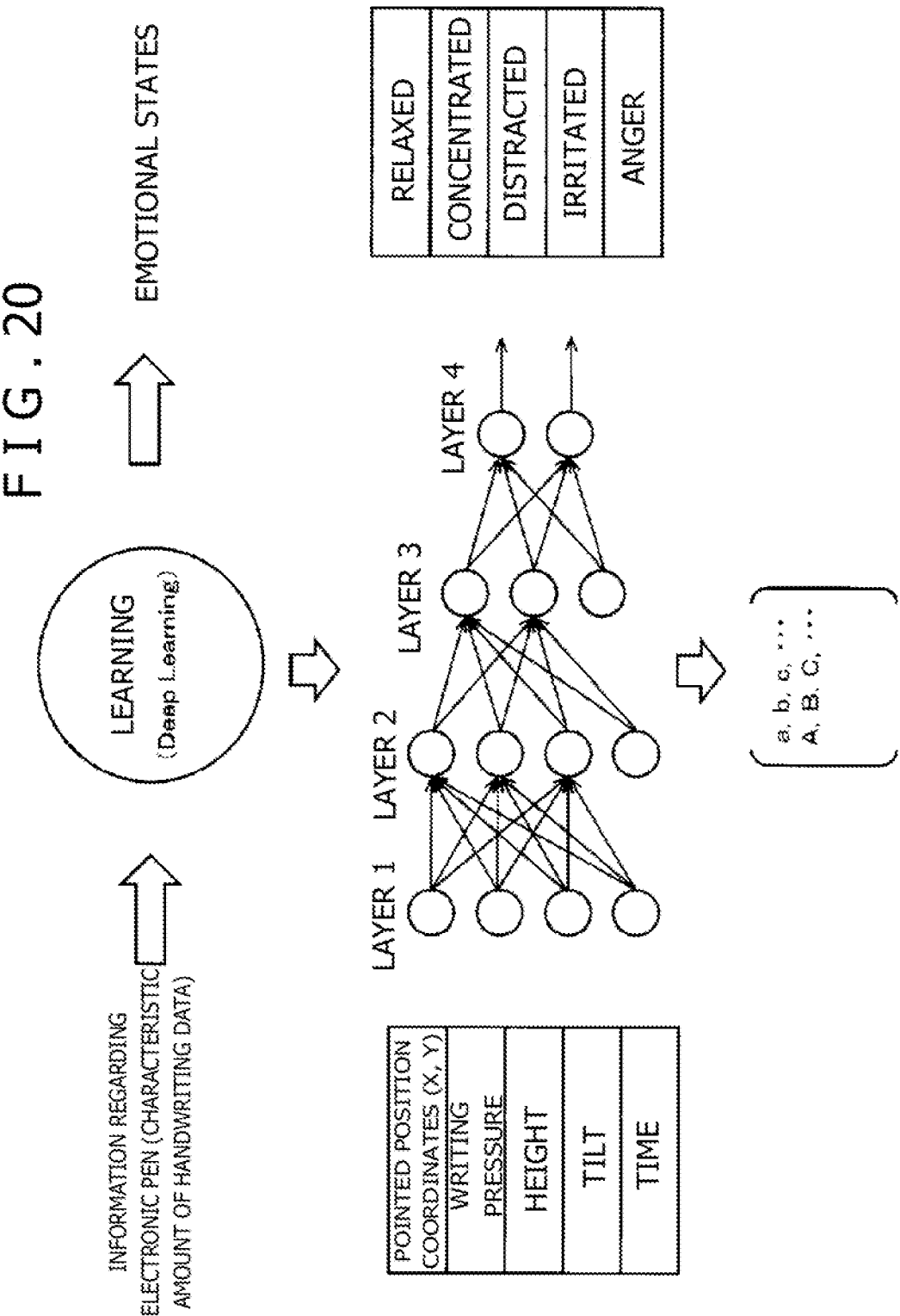

COORDINATE INPUT PROCESSING APPARATUS, EMOTION ESTIMATION APPARATUS, EMOTION ESTIMATION SYSTEM, AND BUILDING APPARATUS FOR BUILDING EMOTION ESTIMATION-ORIENTED DATABASE

BACKGROUND

Technical Field

The present disclosure relates to a coordinate input processing apparatus, an emotion estimation apparatus, an emotion estimation system, and a building apparatus for building an emotion estimation-oriented database.

Background Art

Heretofore, there have been various attempts to estimate a person's emotional state by measuring biological information regarding that person such as his or her brain waves. For example, Patent Document 1 (see Japanese Patent Laid-Open No. 2010-131328) discloses a method and an apparatus for measuring brain waves using a simple electroencephalograph to acquire brain wave information by which to discriminate a person's preference and physiological state.

Patent Document 2 (see Japanese Patent Laid-Open No. 2015-109964) offers a method that involves measuring biological information other than brain waves such as pulse rate and blood flow regarding a target person and, based on the correlation between the measured biological information and brain waves, estimating the target person's brain waves associated with the measured biological information, the estimated brain waves constituting a characteristic pattern that permits estimation of the target person's emotion.

PRIOR ART DOCUMENT

Patent Documents

Patent Document 1: Japanese Patent Laid-Open No. 2010-131328
Patent Document 2: Japanese Patent Laid-Open No. 2015-109964

BRIEF SUMMARY

Technical Problems

Recent years have witnessed the growing use of an electronic pen as an input apparatus for use with electronic equipment. If an emotion of a user using the electronic pen during input work is discriminated (estimated), the user can be offered support corresponding to the discriminated (estimated) emotion, which is convenient.

For example, if the emotion of a worker using electronic pen during input work is discriminated (estimated) to be distracted, the worker may be alerted. If the worker is discriminated (estimated) to be in the emotional state of irritation, it is possible to support the worker by offering emotionally relaxing music to the worker, for example.

To implement the above measures requires discriminating (estimating) the real-time emotional state of the user at the time of input work using the electronic pen. This presumably calls for using the techniques disclosed in the above-cited Patent Documents 1 and 2. However, it is not realistic for the user to wear a simple electroencephalograph and biological information sensors during input work using the electronic pen. Moreover, given the high cost of requiring each worker to wear the simple electroencephalograph and biological information sensors, this may well turn out to be an unrealistic practice.

The present disclosure has been made in view of the above circumstances. An object of the disclosure is therefore to discriminate (estimate) the real-time emotional state of an input worker at the time of input work using an electronic pen without requiring the input worker to wear a simple electroencephalograph or biological information sensors.

Technical Solution

In solving the above problem, the disclosure according to the appended claim 1 provides a coordinate input processing apparatus including: a position detection apparatus that includes a sensor which, in operation, detects a position pointed to by an electronic pen, and circuitry which, in operation, acquires pen state information regarding a state of the electronic pen held by a person; a transmitter which, in operation, transmit to an emotion estimation apparatus an emotional state estimation request including the pen state information acquired by the position detection apparatus, the emotion estimation apparatus including an emotion estimation-oriented information storage device which, in operation, stores information regarding an emotional state of the person holding the electronic pen and range information regarding a range of values that may be taken by the pen state information regarding the state of the electronic pen held by the person at a time of the emotional state, the emotional state and the range information being associated with one another; and a processor which, in operation, receives information corresponding to the emotional state transmitted from the emotion estimation apparatus in response to the pen state information included in the emotional state estimation request transmitted from the transmitter, and performs processing using the received information corresponding to the emotional state.

Also, the disclosure according to the appended claim 8 provides an emotion estimation apparatus including: an emotion estimation-oriented information storage device which, in operation, stores information regarding an emotional state of a person holding an electronic pen and range information regarding a range of values that may be taken by pen state information regarding a state of the electronic pen held by the person at the time of being in the emotional state, the information regarding the emotional state and the range information being associated with one another; and a processor which, upon receipt of an emotional state estimation request including the pen state information regarding the electronic pen, estimates the emotional state of the person holding the electronic pen having transmitted the request information by referencing the emotion estimation-oriented information storage device by use of the received pen state information.

Further, the disclosure according to the appended claim 16 provides a building apparatus that builds an emotion estimation-oriented information storage device, the building apparatus including: at least one processor; and at least one storage device storing processor-readable instructions that, when executed by the at least one processor, cause the building apparatus to: acquire biological information regarding a person performing pointing input using an electronic pen, acquire pen state information regarding the state of the electronic pen held by the person performing the pointing input and associated with the biological information; discriminate an emotional state of the person holding the electronic pen based on the acquired biological information; obtain range information regarding a range of values that may be taken by the pen state information at the time of the discriminated emotional state from the acquired pen state information; and store the discriminated emotional state and the range information regarding the range of values that may be taken by the pen state information into the emotion estimation-oriented information storage device, the discriminated emotional state and the range information being associated with one another.

In general, the hand and fingertips of the worker holding the electronic pen move in a manner reflecting the worker's emotional state at the time of work. Thus the electronic pen held by the worker is at a height position, is tilted relative to the sensor input sur-face, and is under writing pressure in a manner reflecting the worker's emotional state during work. That is, there are correlations between the emotional state of the worker holding the electronic pen on the one hand and the pen state information regarding the state of the electronic pen such as the height position and its variations, the tilt and its variations, and the writing pressure and its variations of the electronic pen on the other hand.

Thus according to the present disclosure, there is provided beforehand the emotion estimation-oriented information storage device that stores the emotional state of the person holding the electronic pen and the range information regarding the range of values that may be taken by the pen state information regarding the state of the electronic pen held by the person at the time of being in the emotional state, the emotion-al state and the range information being associated with one another. The emotion estimation-oriented information storage device, included in the emotion estimation apparatus, has content constituted by the biological information regarding the person performing pointing input using the electronic pen and by the pen state information regarding the state of the electronic pen held by the person associated with the biological information and carrying out the pointing input.

The emotional states here include a relaxed state, a concentrated state, an irritated state, and a distracted state, for example. Used as the pen state information are, for example, the writing pressure and its variations applied to the stylus of the electronic pen, the height position and its variations of the electronic pen relative to the sensor, the tilt and its variations of the electronic pen relative to the sensor surface, and movements in the X and Y axis directions of the sensor not in contact with the electronic pen. What is stored in the emotion estimation-oriented information storage device is the information associating each emotional state with the range information regarding the range of values that may be taken by the pen state information regarding the electronic pen held by the person at the time of being in the emotional state.

The emotion estimation-oriented information storage device may be implemented by the building apparatus that builds an emotion estimation-oriented information storage device according to the appended claim 16. That is, acquired first is the biological information regarding the person performing pointing input using the electronic pen, as well as the pen state information regarding the state of the electronic pen held by the person performing the pointing input and associated with the biological information. The emotional state of the person holding the electronic pen is then discriminated on the basis of the acquired biological information. The range information regarding the range of values that may be taken by the pen state information at the time of the discriminated emotional state is obtained from the acquired pen state information. The discriminated emotional state and the range information regarding the range of values that may be taken by the pen state information are stored into the emotion estimation-oriented information storage device, the discriminated emotional state and the range information being associated with one another.

The coordinate input processing apparatus configured as outlined above according to the appended claim 1 includes the position detection apparatus, transmitter, and processor. The position detection apparatus includes the sensor which, in operation, detects a position pointed by the electronic pen, and acquires the pen state information regarding the state of the electronic pen held by the user. Acquired here as the pen state information are, for example, the writing pressure and its variations applied to the stylus of the electronic pen, the height position and its variations of the electronic pen relative to the sensor, the tilt and its variations of the electronic pen relative to the sensor surface, and movements in the X and Y axis directions of the sensor not in con-tact with the electronic pen, as described above.

The transmitter of the coordinate input processing apparatus according to the appended claim 1 transmits an emotional state estimation request including the acquired pen state information to the emotion estimation apparatus. The disclosure according to the appended claim 8 relates to the emotion estimation apparatus.

That is, with the emotion estimation apparatus according to the appended claim 8, upon receipt of an emotional state estimation request including the pen state information regarding the state of the electronic pen, the emotional state of the user of the electronic pen having transmitted the request information is estimated by referencing the emotion estimation-oriented information storage device by use of the received pen state information. Information corresponding to the estimated emotional state is returned to the coordinate input processing apparatus having made the emotional state estimation request.

Upon receipt of the information corresponding to the estimated emotional state from the emotion estimation apparatus, the coordinate input processing apparatus according to the appended claim 1 performs processing associated with the received information corresponding to the emotional state.

According to the coordinate input processing apparatus of the present disclosure, as outlined above, the emotional state estimation request including the acquired pen state information need only be transmitted to the emotion estimation apparatus. This makes it possible to know the estimated emotional state of the electronic pen user at the time, allowing information processing to be carried out in a manner associated with the emotional state.

Advantageous Effect

The present disclosure provides an advantageous effect of estimating the real-time emotional state of an input worker at the time of input work using the electronic pen without requiring the input worker to wear a simple electroencephalograph or biological information sensors, so that suitable processing is performed to address the estimated emotional state.

BRIEF DESCRIPTION OF DRAWINGS

FIG. 5 is a tabular diagram explaining the example of the building apparatus for building the emotion estimation-oriented information storage device as the embodiment in FIG. 1.

FIG. 6 is a tabular diagram explaining an example of the emotion estimation-oriented information storage device built by the building apparatus for building the emotion estimation-oriented information storage device as the embodiment in FIG. 1.

FIG. 7 is a flowchart explaining a typical flow of operational processing performed by the building apparatus for building the emotion estimation-oriented information storage device as the embodiment in FIG. 1.

FIG. 20 is a schematic diagram explaining key features of the emotion estimation system as yet another embodiment of the present disclosure.

MODES FOR CARRYING OUT THE DISCLOSURE

The preferred embodiments for practicing the present disclosure are described below. Explained first is a building apparatus for building an emotion estimation-oriented information storage device embodying the disclosure.

Figure 1:
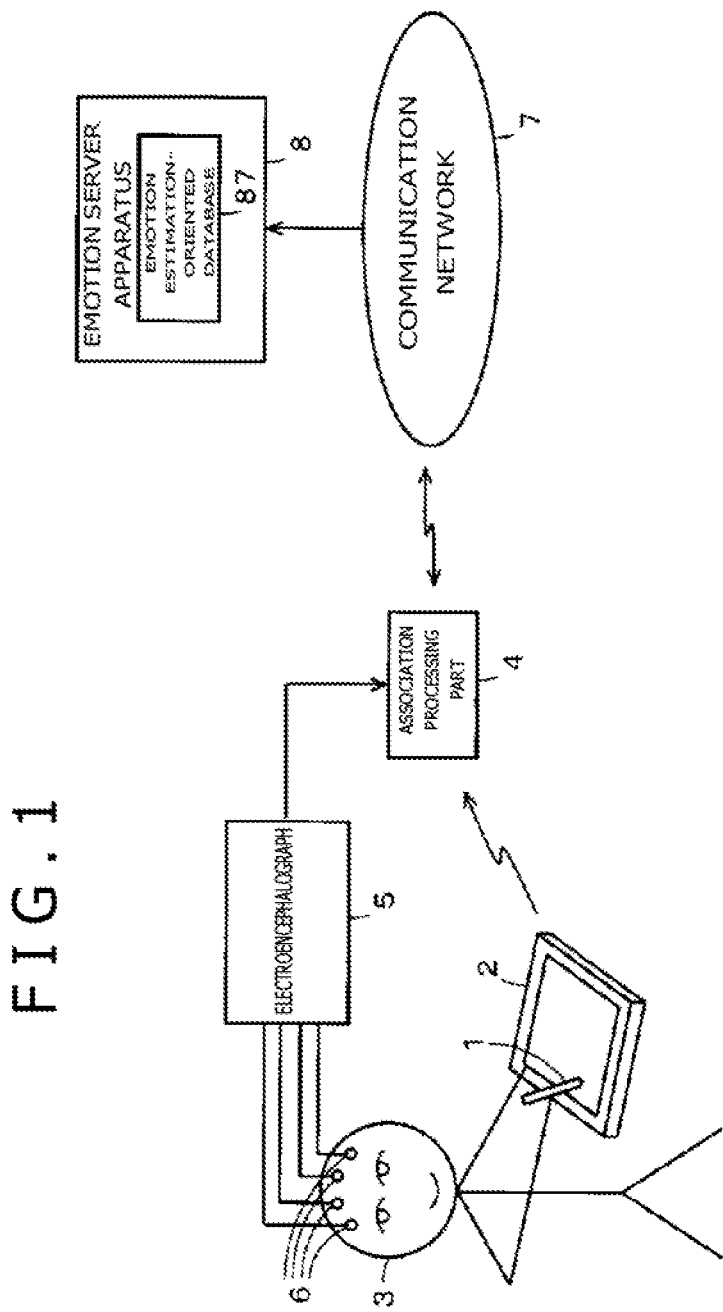
FIG. 1 is a schematic diagram explaining a building apparatus for building an emotion estimation-oriented information storage device as one embodiment of the present disclosure.

First example of the building system for building the emotion estimation-oriented information storage device FIG. 1 outlines a first configuration example of a building system for building an emotion estimation-oriented information storage device including an embodiment of the building apparatus for building the emotion estimation-oriented information storage device. This example is a case in which an electroencephalograph is used to discriminate the emotional state of a person. In the description that follows, the emotion estimation-oriented information storage device will be referred to as the emotion estimation-oriented database.

In the first configuration example, as depicted in FIG. 1, an electronic pen user 3 holding an electronic pen 1 performs pointing input to a tablet terminal 2 equipped with a position detection apparatus that detects pointing input by the electronic pen 1. In this example, the electronic pen 1 and the position detection apparatus of the tablet terminal 2 operate by electromagnetic induction coupling technology.

In this example, the electronic pen 1 has the function of detecting the writing pressure applied to the tip of its stylus. The electronic pen 1 also stores identification information for identifying itself (pen ID). The electronic pen 1 transmits information regarding the detected writing pressure and the pen ID, along with a position detection signal, to the position detection apparatus of the tablet terminal 2. The electronic pen 1 is owned by the user 3, so that the pen ID serves as the identification information identifying the user 3. The writing pressure applied to the electronic pen 1 is detected by known techniques, which will not be discussed further hereunder.

On the basis of the position detection signal from the electronic pen 1, the position detection apparatus of the tablet terminal 2 detects the position pointed by the electronic pen 1 using electromagnetic induction coupling technology. In this example, the electronic pen 1 includes a resonance circuit made up of a coil and a capacitor. The resonance circuit receives an alternating-current signal sent from the position detection apparatus of the tablet terminal 2. The electronic pen 1 feeds the received AC signal as its position detection signal back to the position detection apparatus of the tablet terminal 2.

The electronic pen 1 changes the frequency of the AC signal (resonance frequency) fed from the resonance circuit back to the position detection apparatus of the tablet terminal 2. In so doing, the electronic pen 1 transmits the writing pressure information to the position detection apparatus of the tablet terminal 2. The electronic pen 1 also modulates, by amplitude shift keying (ASK) or by on-off keying (OOK), for example, the AC signal fed from the resonance circuit as a digital signal back to the position detection apparatus of the tablet terminal 2. The position detection apparatus of the tablet terminal 2 acquires the writing pressure information and the pen ID transmitted as described above.

Also in this example, the position detection apparatus of the tablet terminal 2 has the function of detecting the tilt and height position of the electronic pen 1. The tilt of the electronic pen 1 refers to its tilt relative to a sensor surface (position pointing input surface) of the position detection apparatus. The height position of the electronic pen 1 refers to its height position relative to the sensor surface (position pointing input surface) of the position detection apparatus. The tilt and the height position of the electronic pen 1 are detected by known techniques, which will not be discussed further hereunder.

The tablet terminal 2 supplies an association processing device 4 with pen state information made up of the above-described information regarding the detected position pointed by the electronic pen 1, information regarding the writing pressure on the electronic pen 1, information regarding the tilt of the electronic pen 1, and information regarding the height position of the electronic pen 1. In this example, the pen state information regarding the state of the electronic pen includes the information regarding the detected position pointed by the electronic pen, its writing pressure, its tilt, and its height position.

Also in this example, multiple electrodes 6 connected with an electroencephalograph 5 are worn on the head of the electronic pen user 3 so as to discriminate his or her emotional state. The electroencephalograph 5 supplements brain wave data from the electrodes 6 with time information from an internal clock (time in years, months, days, hours, minutes, and seconds), before supplying the brain wave data to the association processing device 4.

The association processing device 4 is constituted by a personal computer, for example. The association processing device 4 acquires from the tablet terminal 2 the information regarding the position pointed by the electronic pen, the pen ID, and the pen state information while obtaining the brain wave data from the electroencephalograph 5 at the same point in time, associates the acquired items of information with one another, and adds a timestamp (time information at that point in time in years, months, days, hours, minutes, and seconds) to the mutually associated information. The association processing device 4 transmits the mutually associated information combined with the timestamp to an emotion server apparatus 8 via a communication network 7.

The communication network 7 may be configured with the Internet and public networks including mobile telephone networks. Alternatively, the communication network 7 may be a wireless local area network (LAN) that uses Wireless Fidelity (Wi-Fi) (registered trademark). As another alternative, the communication network 7 may be a wired LAN connecting the emotion server apparatus 8 with the association processing device 4 by wire.

The emotion server apparatus 8 receives information from the association processing device 4, and acquires from the received information the pen ID of the electronic pen 1, the brain wave data, and the pen state information regarding the electronic pen 1 in a manner separate from one another. Of the received information, the brain wave data from the electroencephalograph 5 is used to discriminate (verify) the emotional state of the user of the electronic pen 1 at the current point in time. In this example, a "relaxed state," a "concentrated state," an "irritated state," a "distracted state," or an "angry state" is discriminated (verified) as the emotional state. Well-known methods of discriminating these emotional states from brain wave data involve, for example, finding the ratio of frequency components (frequency distribution) of α waves, β waves and θ waves constituting the brain waves for discrimination in accordance with such findings.

The emotion server apparatus 8, as will be discussed later, calculates range information regarding a range of values that may be taken by the pen state information in each of the emotional states discriminated with regard to the user of the electronic pen 1 on the basis of the information received from the tablet terminal 2.

The emotion server apparatus 8 then stores each discriminated emotional state, the range information regarding the range of values that may be taken by the pen state information in that emotional state, and the pen ID of the electronic pen in a manner associating them with one another in an internal emotion estimation-oriented database.

Typical electric circuit configurations of the electronic pen 1 and the position detection apparatus of the tablet terminal 2

Figure 2:
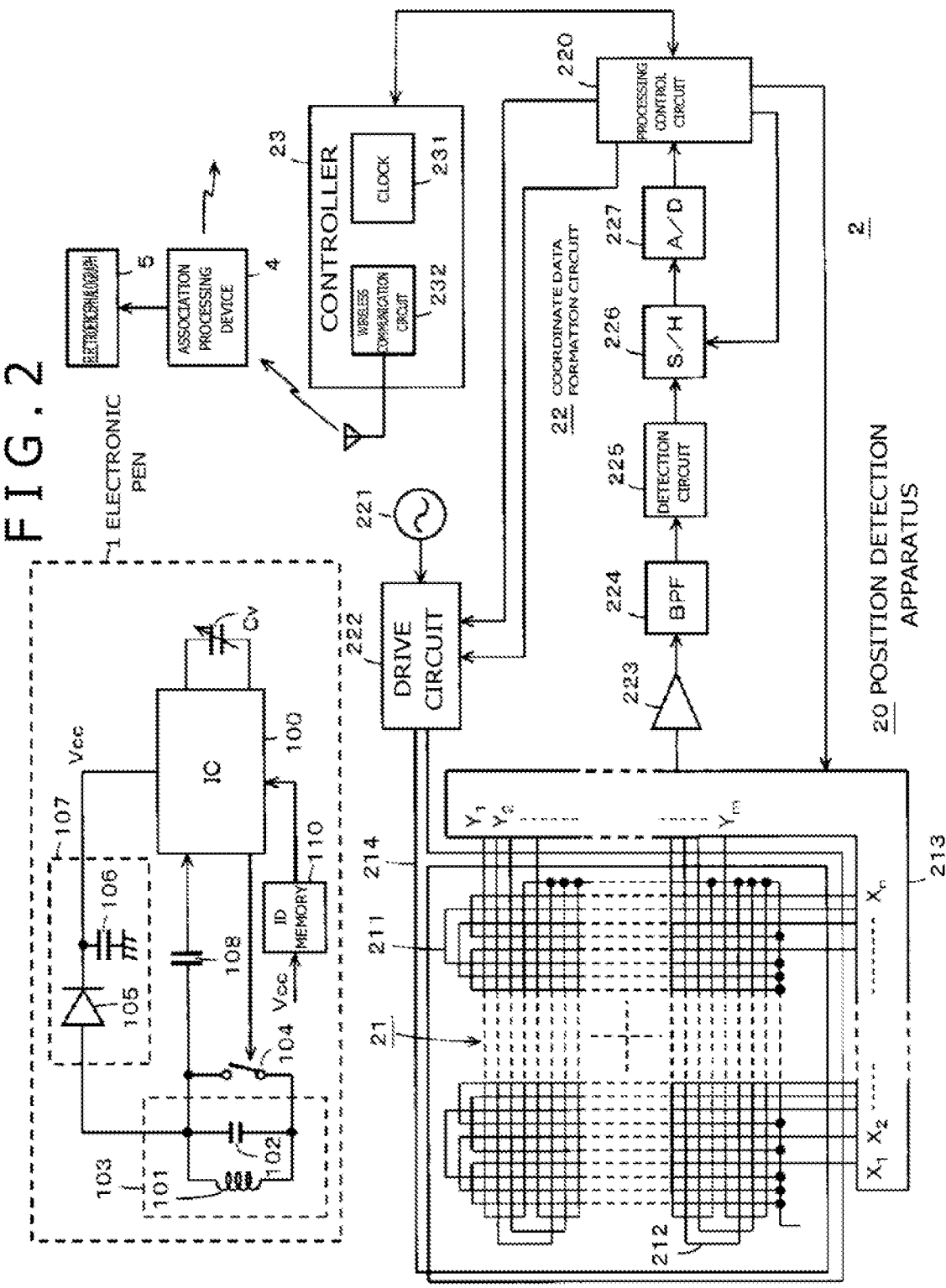
FIG. 2 is a schematic diagram depicting typical electric circuit configurations of an electronic pen and a tablet terminal making up the embodiment in FIG. 1.

FIG. 2 depicts typical circuit configurations of an equivalent circuit of the electronic pen 1 and a position detection apparatus 20 of the tablet terminal 2 in a first example, the position detection apparatus 20 performs position detection and writing pressure detection in conjunction with the electronic pen 1 using electromagnetic induction coupling technology.

The position detection apparatus 20 of the tablet terminal 2 in the example of FIG. 2 includes a sensor 21, a coordinate data formation circuit 22, and a controller 23. The sensor 21 is formed with an X-axis direction loop coil group 211 and a Y-axis direction loop coil group 212 stacked one on top of the other, as well as a selection circuit 213 for successively selecting each of the loop coils making up the two loop coil groups 211 and 212.

The electronic pen 1 has a signal control circuit constituted by an IC 100. The electronic pen 1 is also configured in such a manner that a drive voltage for driving the IC 100 is acquired from an excitation signal transmitted from an exciting coil 214 included in the sensor 21 of the position detection apparatus 20 in the tablet terminal 2. With the example in FIG. 2, it is explained here that the X-axis direction loop coil group 211 and Y-axis direction loop coil group 212 are used solely to receive an electromagnetic coupling signal from the electronic pen 1. However, this does not exclude driving the signal control circuit in the electronic pen 1 by use of the electromagnetic coupling with the pen 1 in place of the exciting coil 214. Also, transmission of signals such as predetermined control data to the signal control circuit in the electronic pen 1 is not excluded.

In the sensor 21 of the position detection apparatus 20 in the tablet terminal 2 in the example in FIG. 2, the exciting coil 214 is arranged to surround the X-axis direction loop coil group 211 and Y-axis direction loop coil group 212. Although FIG. 2 depicts the exciting coil 214 having 2 turns, the number of turns is larger in practice, amounting to 8 to 10 turns, for example. As illustrated in FIG. 2, the exciting coil 214 is connected with a drive circuit 222 that in turn is connected with an oscillation circuit 221 oscillating at a frequency of fo.

The drive circuit 222 is controlled by a processing control circuit 220 formed by a microcomputer. The processing control circuit 220 controls the drive circuit 222 to adjust the supply of an oscillation signal at the frequency fo from the oscillation circuit 221 to the exciting coil 214, thereby controlling the signal transmission from the exciting coil 214 to the electronic pen 1.

The selection circuit 213 selects one loop coil under selection control of the processing control circuit 220. An induced voltage developed on the loop coil selected by the selection circuit 213 is amplified by a receiving amplifier 223. The amplified voltage is supplied to a band-pass filter 214 where only the component having the frequency fo is extracted. The band-pass filter 214 supplies the extracted component to a detection circuit 225.

The detection circuit 225 detects the component at the frequency fo, and supplies a sample-hold circuit 226 with a direct-current signal corresponding to the detected component having the frequency fo. The sample-hold circuit 226 holds a voltage value at a predetermined timing of the output signal from the detection circuit 225. Specifically, the sample-hold circuit 226 holds the voltage value at the predetermined timing during a reception period, before outputting the voltage value to an AD conversion circuit 227. The AD conversion circuit 227 converts the analog output from the sample-hold circuit 226 into a digital signal, and outputs the digital signal to the processing control circuit 220. The processing control circuit 220 supplies the above-mentioned signal obtained at the predetermined timing to the sample-hold circuit 226.

The processing control circuit 220 discriminates whether the digital signal from the AD conversion circuit 227 exceeds a predetermined threshold value, thereby determining whether the loop coil selected by the selection circuit 213 is the loop coil at the position pointed by the electronic pen 1. On the basis of the discrimination, the processing control circuit 220 detects the position pointed by the electronic pen 1.

Apart from detecting the position pointed by the electronic pen 1, the processing control circuit 220 also detects the connection and disconnection of signals from the electronic pen 1 in the form of a digital signal of multiple bits so as to detect the writing pressure as well as the pen ID, as will be discussed later. The processing control circuit 220 supplies the controller 23 with information regarding the position pointed by the electronic pen, information regarding the detected writing pressure, and the detected pen ID in such a manner that these items of information are associated with one another.

The controller 23 stores into a buffer, not depicted, the received information regarding the position pointed by the electronic pen, the received information regarding the writing pressure, and the received pen ID. The controller 23, furnished with a clock 231 having a calendar function, also stores into the buffer time information in years, months, days, hours, minutes, and seconds regarding the point in time at which the pointed position information, writing pressure information, and pen ID were received in a mutually associated manner.

The controller 23 further transmits the pointed position information, the writing pressure information, the pen ID, and the time information stored in the buffer to the association processing device 4 via a wireless communication circuit 232.

The circuit configuration of the electron pen 1 is enclosed with broken lines as illustrated in FIG. 2. That is, a resonance circuit 103 is configured with a capacitor 102 connected in parallel with a coil 101 acting as an inductance element. The resonance circuit 103 is connected in parallel with a switch circuit 104. The switch circuit 104 is configured to be turned on and off under control of the IC 100. When the switch circuit 104 is turned off, the resonance circuit 103 resonates with the signal from the sensor 21. When the switch circuit 104 is turned on, the capacitor 102 connected in parallel with the coil 101 is short-circuited so that the resonance circuit 103 stops resonating with the signal from the sensor 21.

The IC 100 is configured to operate on a power supply voltage Vcc obtained by having an AC signal rectified by a rectifier circuit (power supply circuit) 107 made of a diode 105 and a capacitor 106, the AC signal being received through electromagnetic induction with the resonance circuit 103 from the sensor 21 of the position detection apparatus 20 in the tablet terminal 2. The IC 100, connected with the resonance circuit 103 via a capacitor 108, monitors the operating state of the resonance circuit 103. By monitoring the operating state of the resonance circuit 103, the IC 100 detects either the state of electromagnetic coupling with the exciting coil 214 of the sensor 21 or signals such as control data sent from the sensor 21 of the position detection apparatus 20 using the two loop coil groups 211 and 212, not explained here, so as to perform desired operation controls.

The electronic pen 1 of this embodiment includes a writing pressure detection means formed by pressure sensitive elements that detect the writing pressure applied to the stylus as the capacitance of a variable capacitor Cv, for example. As depicted in FIG. 2, the IC 100 connected with the variable capacitor Cv is configured to detect the capacitance thereof reflecting the writing pressure. The IC 100 thus detects the writing pressure to the electronic pen 1 from the capacitance value of the variable capacitor Cv. The IC 100 converts the detected writing pressure to a digital signal in multiple bits, and controls the switch circuit 104 in accordance with the digital signal corresponding to the writing pressure. In so doing, the IC 100 transmits the information regarding the writing pressure to the position detection apparatus 20 of the tablet terminal 2 in the form of information added to the position detection signal.

The IC 100 is also connected with an ID memory 110 that stores the pen ID serving as identification information identifying the electronic pen 1. Using a digital signal stored in the ID memory 110, the IC 100 controls the switch circuit 104 to transmit the pen ID to the position detection apparatus 20 of the tablet terminal 2 also in the form of information added to the position detection signal together with the writing pressure information.

Described below are the operations performed by the electronic pen 1 and by the position detection apparatus 20 of the tablet terminal 2, both configured as explained above, in order to detect the position, the writing pressure information, and the pen ID of the electronic pen 1.

First, the processing control circuit 220 drives the drive circuit 222 to transmit a signal from the exciting coil 214 to the electronic pen 1 for a predetermined time. The processing control circuit 220 then drives the drive circuit 222 to output a burst-type signal from the exciting coil 214. Thereafter, the processing control circuit 220 performs the process of causing the selection circuit 213 to successively select each of all loop coils making up the X-axis direction loop coil group 211. The electronic pen 1 causes the resonance circuit 103 to receive the burst-type signal and feeds the received signal back to the sensor 21 of the position detection apparatus 20 in the tablet terminal 2. By detecting the feedback burst-type signal as the position detection signal, the processing control circuit 220 obtains the X-coordinate value of the position pointed by the electronic pen 1.

Next, the processing control circuit 220 drives the drive circuit 222 to transmit a signal from the exciting coil 214 to the electronic pen 1 for a predetermined time. The processing control circuit 220 then drives the drive circuit 222 to output a burst-type signal from the exciting coil 214. Thereafter, the processing control circuit 220 performs the process of causing the selection circuit 213 to successively select each of all loop coils making up the Y-axis direction loop coil group 212. The electronic pen 1 causes the resonance circuit 103 to receive the burst-type signal and feeds the received signal back to the sensor 21 of the position detection apparatus 20 in the tablet terminal 2. By detecting the feedback burst-type signal as the position detection signal, the processing control circuit 220 obtains the Y-coordinate value of the position pointed by the electronic pen 1.

When the position pointed by the electronic pen 1 is detected as described above, the processing control circuit 220 causes a signal to be transmitted from the exciting coil 214 for a predetermined time in order to detect the writing pressure information and pen ID as the added information from the electronic pen 1. Thereafter, the processing control circuit 220 continuously performs signal transmission and reception at the same timing as upon coordinate detection as many times as the number of bits constituting the digital signal carrying the added information. At this point, the selection circuit 213 selects the loop coil (either an X-axis or a Y-axis direction loop coil) closest to the electronic pen 1 in accordance with the detected coordinate values for signal reception.

Meanwhile, the IC 100 of the electronic pen 1 puts the switch circuit 104 under on-off control in synchronism with the signal transmission and reception to and from the position detection apparatus 20 of the tablet terminal 2 using the added information in the form of the digital signal formed by the pen ID and the writing pressure information obtained as representative of the capacitance of the variable capacitor Cv making up the writing pressure detection means. When the switch circuit 104 is turned off, the resonance circuit 103 returns to the position detection apparatus 20 the signal transmitted therefrom. The loop coil of the position detection apparatus 20 receives the returned signal. On the other hand, when the switch circuit 104 is turned on, the resonance circuit 103 is inhibited from oscillating. The resonance circuit 103 thus does not return the signal to the position detection apparatus 20, so that the loop coil of the position detection apparatus 20 does not receive the signal.

The processing control circuit 220 of the coordinate data formation circuit 22 in the position detection apparatus circuit 20 discriminates the presence or absence of the received signal as many times as the number of bits making up the digital signal constituting the added information. In so doing, the processing control circuit 220 receives the digital signal in multiple bits reflecting the writing pressure information and the pen ID, thereby detecting the writing pressure information and the pen ID from the electronic pen 1. The electronic pen 1 thus transmits the writing pressure information and the pen ID as an ASK modulated signal to the position detection apparatus 20 of the tablet terminal 2.

The processing control circuit 220 of the position detection apparatus 20 detects the information regarding the position pointed by the electronic pen 1 as well as the writing pressure information and the pen ID from the electronic pen 1. The processing control circuit 220 then supplies the controller 23 with the detected position pointed by the electronic pen 1, the detected writing pressure information, and the detected pen ID. The controller 23 adds time information to the position pointed by the electronic pen 1, to the writing pressure information, and to the pen ID following their receipt from the processing control circuit 220 and causes the wireless communication circuit 232 to transmit the combined information to the association processing device 4.

The association processing device 4 associates the position pointed by the electronic pen 1, the writing pressure information, and the pen ID following their receipt from the tablet terminal 2 with the brain wave data from the electroencephalograph 5 on the basis of the time information added to such data and information. The association processing device 4 then adds corresponding time information to the mutually associated information and transmits the combined information to the emotion server apparatus 8 via the communication network 7.

<Typical Configuration of the Emotion Server Apparatus 8>

Figure 3:
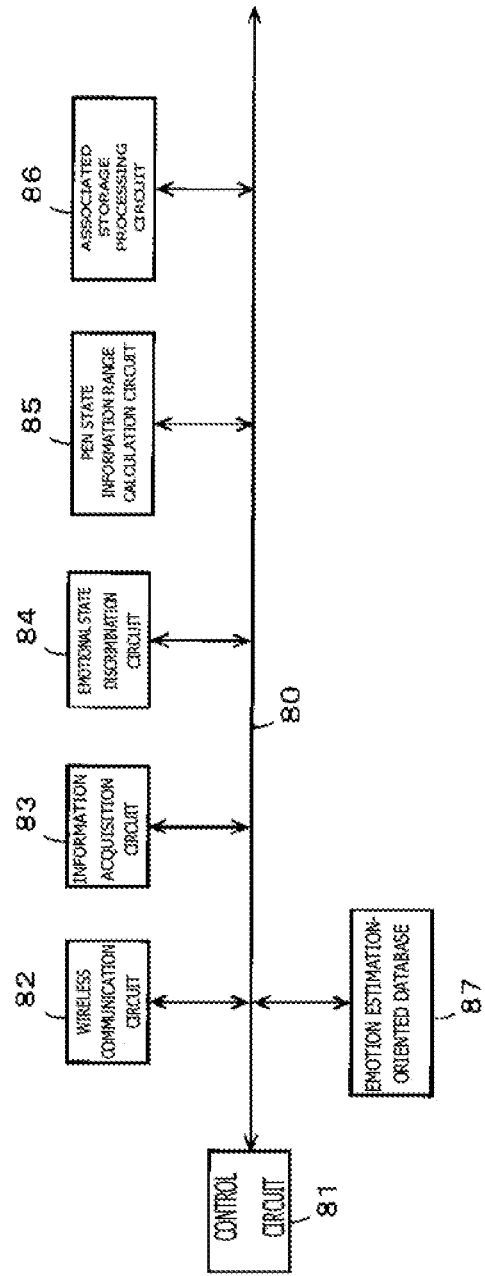
FIG. 3 is a block diagram depicting a typical configuration of an emotion server apparatus making up the embodiment in FIG. 1.

FIG. 3 depicts a typical configuration of the emotion server apparatus 8 making up this embodiment. That is, the emotion server apparatus 8 is configured with a control circuit 81 formed by a computer, the control circuit 81 being connected with a wireless communication circuit 82, an information acquisition circuit 83, an emotional state discrimination circuit 84, a pen state information range calculation circuit 85, an associated storage processing circuit 86, and an emotion estimation-oriented database 87 via a system bus 80.

The control circuit 81 provides overall control of the emotion server apparatus 8. The wireless communication circuit 82, which communicates wirelessly via the communication network 7, receives information from the association processing device 4 in this example. From the information received through the wireless communication circuit 82, the information acquisition circuit 83 extracts and acquires information associating the position pointed by the electronic pen 1, the writing pressure information, and the pen ID from the tablet terminal 2 with the brain wave data from the electroencephalograph 5, together with the timestamp.

With the information thus acquired, the information acquisition circuit 83 supplies the brain wave data from the electroencephalograph 5 and the pen ID to the emotional state discrimination circuit 84. The information acquisition circuit 83 further supplies the position pointed by the electronic pen, the writing pressure information, and the pen ID from the tablet terminal 2 to the pen state information range calculation circuit 85.

Given the brain wave data over a predetermined time, the emotional state discrimination circuit 84 discriminates the user's emotional state at that time. The pen state information range calculation circuit 85 calculates a range of electronic pen coordinate position blur, a range of writing pressures, a range of tilts, and a range of height positions at the time of the discriminated emotional state. The emotional state discrimination circuit 84 supplies the discriminated emotional state to the associated storage processing circuit 86 together with the pen ID. The pen state information range calculation circuit 85 supplies the range of coordinate position bur of the electronic pen 1, the range of writing pressures, the range of tilts, and the range of height positions all calculated at the time of the discriminated emotional state to the associated storage processing circuit 86 together with the pen ID.

The associated storage processing circuit 86 associates the received information regarding the emotional state and the respective ranges of pen state information with the pen ID, before storing the mutually associated information into the emotion estimation-oriented database 87.

As described above, the "relaxed state," "concentrated state," "irritated state," "distracted state," or "angry state" is discriminated as the emotional state. Discrimination of the emotional state is accomplished by analyzing biological information, or the brain wave data in this example. With this embodiment, the user 3 of the electronic pen 1 targeted for emotional state discrimination is brought into each of the "relaxed state," "concentrated state," "irritated state," "distracted state," and "angry state" continuously for at least a predetermined time period under contextual stimulus, for example, the emotional state being verified through measurement by the electroencephalograph 5.

For example, the user 3 of the electronic pen 1 is given the conceptual stimulus such as the type of music that soothes the user 3 for a predetermined time in order to reach the "relaxed state." The "concentrated state" is reached by the user 3 invited to write or draw favorite calligraphy or pictures in a focused manner for a predetermined time. The "irritated state" is reached by the user 3 receiving the contextual stimulus such as being deliberately pressed to perform input operations with the electronic pen 1. In such a manner, the user is put into each of the "relaxed state," "concentrated state," "irritated state," "distracted state," and "angry state." The brain wave data about the user in each of these emotional states is measured by the electroencephalograph 5, the measurements being used to verify that the user is in each emotional state.

In such cases, $\alpha$, $\beta$, and $\theta$ waves, for example, are measured and recorded as the brain wave data. The measurements of these waves are then checked, for example, for distribution shapes to discriminate or verify which of the above emotional states the user is in. That is, there exist correlations between the distribution shapes of $\alpha$, $\beta$, and $\theta$ brain waves on the one hand and the emotional states on the other hand. A database of these correlations, not illustrated, is included in the emotional state discrimination circuit 84 of the emotion server apparatus 8. The emotional state discrimination circuit 84 of the emotion server apparatus 8 references the correlation database by use of the distribution shape of $\alpha$, $\beta$, and $\theta$ waves in the brain wave measurements so as to estimate, discriminate, or verify the emotional state of the user 3.

What follows is an example of the method by which each of the "relaxed state," "concentrated state," "irritated state," "distracted state," and "angry state" is artificially brought about; the user is verified and discriminated to be in each of these emotional states based on brain wave data; the pen state in each of these emotional states is measured; and the measurements are stored as data.

Figure 4:
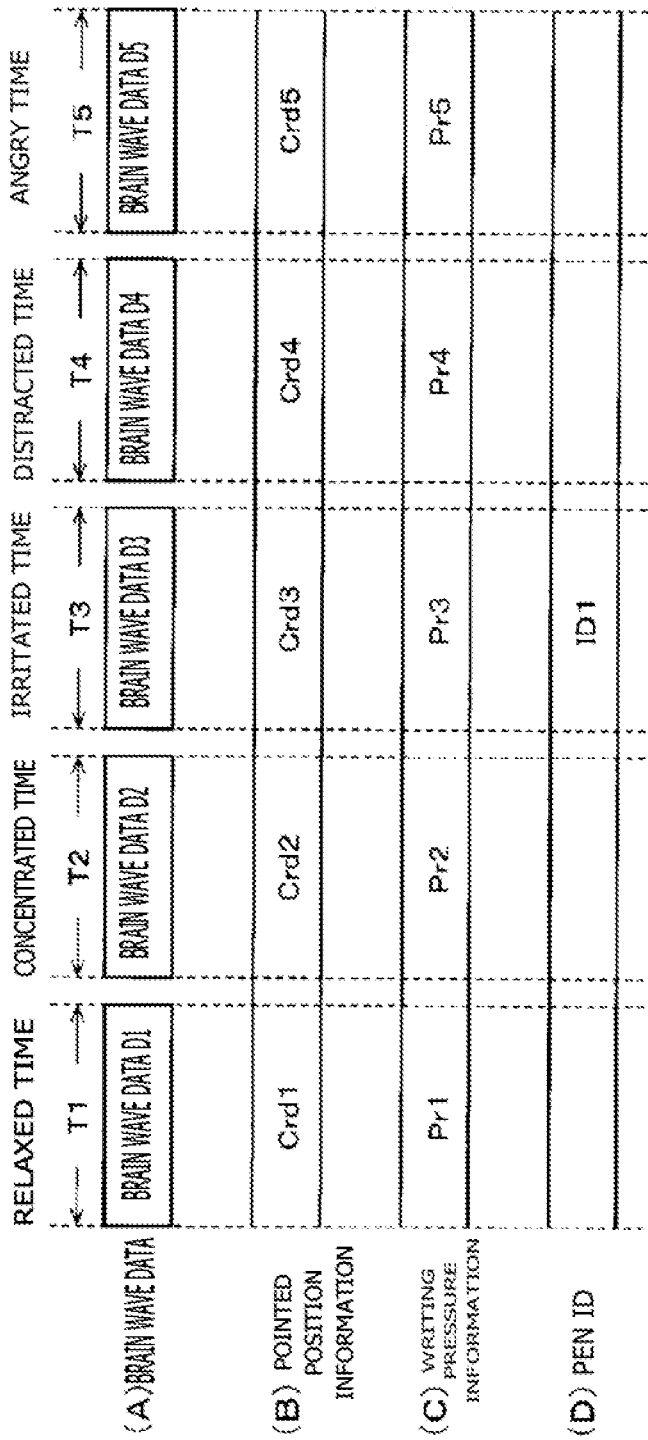
FIG. 4 is a schematic diagram explaining an example of the building apparatus for building the emotion estimation-oriented information storage device as the embodiment in FIG. 1.

In this example, as depicted in Subfigure (A) in FIG. 4, the electroencephalograph 5 generates predetermined times T1, T2, T3, T4, and T5 in which the user of the electronic pen 1 is in the "relaxed state," "concentrated state," "irritated state," "distracted state," and "angry state" respectively, and generates brain wave data D1, D2, D3, D4, and D5 associated with the respective emotional states in the respective predetermined times T1, T2, T3, T4, and T5. The predetermined times T1, T2, T3, T4, and T5 are each arranged to be long enough for the emotion server apparatus 8 to discriminate (verify) each of the "relaxed state," "concentrated state," "irritated state," "distracted state," and "angry state" as the emotional state.

Then as illustrated in Subfigures (B) and (C) in FIG. 4, in the predetermined times T1, T2, T3, T4, and T5, the tablet terminal 2 detects information Crd1, Crd2, Crd3, Crd4, and Crd5 regarding the position pointed by the electronic pen 1 and writing pressure information Pr1, Pr2, Pr3, Pr4, and Pr5, respectively, when the electronic pen user is in the "relaxed state," "concentrated state," "irritated state," "distracted state," and "angry state" respectively. As depicted in Subfigure (D) in FIG. 4, the tablet terminal 2 acquires the same pen ID (=ID1) for all predetermined times T1, T2, T3, T4, and T5. In each of the predetermined times T1, T2, T3, T4, and T5, the tablet terminal 2 detects not only the information regarding the position pointed by the electronic pen 1 but also the pen state information such as the tilt and height position of the electronic pen 1. As discussed above, the information regarding the position pointed by the electronic pen 1 and the pen state information such as writing pressure information, tilt and height position are transmitted from the tablet terminal 2 together with the associated pen ID to the emotion server apparatus 8 via the association processing device 4.

Thus the emotional state discrimination circuit 84, given the brain wave data in the predetermined times T1, T2, T3, T4, and T5, verifies that the user 3 is in the "relaxed state," "concentrated state," "irritated state," "distracted state," and "angry state," respectively.

The pen state information range calculation circuit 85 then calculates a range in which is present each of multiple items of pen state information associated with the "relaxed state," "concentrated state," "irritated state," "distracted state," and "angry state" as the user's emotional states over the predetermined times T1, T2, T3, T4, and T5, respectively. That is, each of the pen states of the electronic pen 1 held by the user in each of the emotional states constitutes a corresponding presence range that is to be calculated. For example, the writing pressure applied to the electronic pen 1 in the "relaxed state" takes on the presence range of values of which the mean value is relatively low, with deviations from the mean value being relatively small. Also, the writing pressure applied to the electronic pen 1 in the "irritated state" takes on the presence range of values of which the mean value is relatively high, with deviations from the mean value being relatively high.

In this example, the "range of tilts," "range of height positions," and "range of pen tip position blur in a hovering state" are calculated from the information regarding the position (see Subfigure (B) in FIG. 4) pointed by the electronic pen 1 (including its height position). Also, the "range of writing pressures (at the time of writing)" is calculated from the writing pressure information (see Subfigure (C) in FIG. 4) regarding the electronic pen 1. Incidentally, the range information regarding a range of pen state information is calculated by discriminating the range in which most, or 90 percent, for example, of the pen state information values fall or are present over at least a predetermined time needed to discriminate the emotional state. Here, the percentage of values that fall in the range of pen state information at the time of calculating the range information regarding the pen state information is related to the accuracy in estimating the emotional state from the pen state information. It is obvious that the higher the percentage, the higher the accuracy of the estimated emotional state. The range information made up of the above-mentioned mean value and deviations may be regarded as the range information regarding the range of pen state information (i.e., presence range information).

With this embodiment, the range information regarding the range of pen state information associated with each emotional state is detected in real time. Alternatively, the pen state information acquired in the above-mentioned predetermined times T1, T2, T3, T4, and T5 may be stored, and the stored pen state information may be subsequently used to calculate the respective range information.

With this embodiment, the pen state information range calculation circuit 85 further stores a "characteristic pattern at the time of writing characters" in each emotional state of the user 3 of the electronic pen 1. Thus in this example, the user 3 as the target from which to acquire brain wave data is requested to write a predetermined character inside a predetermined square region in each emotional state.

That is, as depicted in FIG. 5, the user 3 is presented with a character input square frame FL on the display screen of the tablet terminal 2. The user 3 is prompted to write a character in that character input square frame FL. As illustrated in FIG. 5, the user 3 in each emotional state writes a character requested for input, e.g., a Japanese Hiragana character "あ" inside the input square frame FL using the electronic pen 1.

As depicted in FIG. 5, the user 3 in the relaxed or concentrated state writes the requested character neatly inside the input square frame FL. That is, the center position of the character is close to the center position of the input square frame FL, with the size of the character not exceeding the input square frame FL.

On the other hand, in the irritated, distracted, or angry state, the character center position deviates accordingly from the center position of the input square frame FL, and the size of the character exceeds partly or largely the input square frame FL in accordance with the emotional state. The pen state information range calculation circuit 85 may then calculate, in accordance with each emotional state, the range of deviations from the character center position and the range of character size variations as the characteristic pattern at the time of writing as typical of the pen state information.

Alternatively, characteristic patterns of not only one character but also consecutively written multiple characters may be calculated as the "characteristic pattern at the time of writing." In this case, the range of deviations of multiple characters from their character center position and the range of size variations of multiple characters, for example, may be calculated as the characteristic pattern.

The pen state information range calculation circuit 85 supplies the associated storage processing circuit 86 with the range information regarding the range of pen state information calculated as described above for each of the predetermined times T1, T2, T3, T4, and T5 in which the respective emotional states were detected.

The associated storage processing circuit 86 associates the information regarding the emotional states discriminated by the emotional state discrimination circuit 84 in the predetermined times T1, T2, T3, T4 and T5, with the range information regarding the range of each of multiple items of pen state information from the pen state information range calculation circuit 85 as well as with the pen ID. The associated storage processing circuit 86 stores the mutually associated information into the emotion estimation-oriented database 87.

FIG. 6 depicts an example of stored content in the emotion estimation-oriented database 87 at this point. As illustrated in FIG. 6, the "relaxed," "concentrated," "irritated," "distracted," and "angry" emotional states are stored in association with pen IDs identifying electronic pen users. Also, the information regarding the range that may be taken by the pen state information in each of the emotional states is stored in association with the respective emotional states.

In the example of FIG. 6, a "coordinate pointing blur," a "writing pressure," a "tilt," a "height position," and a "hovering position blur" at the time of input by writing are stored as the pen state information. Stored as the coordinate pointing blur are the range of deviations from the character center position and the range of character size variations explained above with reference to FIG. 5. FIG. 6 schematically depicts the deviation range and the size variation range. The square frames indicated in FIG. 5 each correspond to the above-described squire frame FL in FIG. 5.

In the case of "coordinate pointing blur," the speed or acceleration of the blur changes mildly or violently in keeping with the emotional state. Information regarding these changes may also be stored into the emotion estimation-oriented database 87.

The range of writing pressures (e.g., Pra1 to Prb1) is stored as the "writing pressure" because the user is expected to apply different writing pressures to the electronic pen 1 when making input onto the sensor with the pen 1. For example, the writing pressure in the concentrated state is larger than in the relaxed state, and the range of writing pressures in the concentrated state is smaller than in the relaxed state. In the irritated state, writing pressures are diverse, so that the range of writing pressures is extensive. In the angry state, the writing pressure tends to be higher. Not only the range of writing pressures but also their mean value may be stored at the same time. The change in writing pressure over time may also be stored into the emotion estimation-oriented database 87. For example, the change in writing pressure over time is smaller in the "relaxed state" and "concentrated state" and is larger in the "irritated state" and "distracted state."

The "tilt" of the electronic pen 1 relative to the sensor surface (input surface) varies with the user's emotional state. The range of such tilts with respect to each emotional state is thus stored into the emotion estimation-oriented database 87. Also in this case, the change in tilt over time may be stored into the emotion estimation-oriented database 87 at the same time. For example, the change in tilt over time is small in the "relaxed state" or "concentrated state" and is pronounced in the "irritated state" or "distracted state." Alternatively, the tilts may be stored into the emotion estimation-oriented database 87 in two separate cases: where the writing pressure is zero and the electronic pen is in the hovering state, and where the writing pressure is higher than 0 with the electronic pen in contact with the sensor surface.

The "height position" is taken by the electronic pen 1 held by the user 3 in the hovering state waiting for pointing input (i.e., input by writing) in each of the user's emotional states in a direction perpendicular to the sensor surface. Information regarding the range of such height positions is stored into the emotion estimation-oriented database 87.

The "hovering position blur" is incurred by the electronic pen 1 held by the user 3 in a wait state prior to pointing input (input by writing) as changes in the coordinate position on the sensor surface. That is, the "hovering position blur" is small when the user is in the "concentrated state" and is pronounced when the user is in the "irritated state" or "distracted state," for example. Also in this case, the changes in hovering position blur over time may be stored into the emotion estimation-oriented database 87 at the same time.

As described above, this embodiment causes the emotion estimation-oriented database 87 to store each item of range information regarding the range of pen state information in association with each emotional state of the user identified by the pen ID.

This embodiment also allows the emotion estimation-oriented database 87 to store the range information regarding ranges of general pen state information targeted for the general user in association with each of the "relaxed," "concentrated," "irritated," "distracted," and "angry" emotional states. This is intended to estimate the emotional state of not only the user identified by the pen ID stored in the emotion estimation-oriented database 87 but also all electronic pen users. The pen state information range calculation circuit 85 calculates the range information regarding each of the ranges of general pen state information by performing, for example, the process of averaging each of the ranges of pen state information in association with each of the emotional states of numerous users stored in conjunction with their pen IDs stored in the emotion estimation-oriented database 87.

The emotion server apparatus 8 above may also be configured to let the information acquisition circuit 83, emotional state discrimination circuit 84, pen state information range calculation circuit 85, and associated storage processing circuit 86 be implemented by the control circuit 81 executing programs stored in an internal storage device to function as a software function processing module performing these processes.

<Process of Building the Emotion Estimation-Oriented Database by the Emotion Server Apparatus 8>

FIG. 7 is a flowchart explaining a typical flow of processing performed by the emotion server apparatus 8 for building the emotion estimation-oriented database. The example in FIG. 7 is explained on the assumption that the control circuit 81 of the emotion server apparatus 8 acting as the software function processing module implements the information acquisition circuit 83, emotional state discrimination circuit 84, pen state information range calculation circuit 85, and associated storage processing circuit 86. Incidentally, FIG. 7 depicts the flow of typical processing for generating the information to be stored into the emotion estimation-oriented database regarding a single user 3. That means the processing in FIG. 7 may also be performed on a different user who may take the place of the current user.

In this example, the predetermined times T1, T2, T3, T4, and T5 are executed successively as the periods in which to discriminate the user's emotional states as illustrated in FIG. 4.

First, the control circuit 81 receives information associating the brain wave data with the electronic pen state information (including information about the position pointed by the electronic pen 1) via the communication network 7 (S101). From the acquired brain wave data, the control circuit 81 discriminates the emotional state of the user 3 associated with the pen ID (S102). S102 involves executing the process of discriminating the user's emotional state in one of the predetermined times T1, T2, T3, T4, and T5 mentioned above.

The control circuit 81 then detects a range of values corresponding to the emotional state discriminated at S102 with respect to each item of electronic pen state information (S103). The control circuit 81 discriminates whether the range of values can be detected regarding each item of electronic pen state information (104). If it is discriminated that the range of values is not detected, the control circuit 81 further receives information from the association processing device 4 via the communication network 7 (S105). Thereafter, the control circuit 81 returns control to S103 and repeats the subsequent steps.

If it is discriminated at S104 that the range of values is detected for each item of electronic pen state information, the control circuit 81 stores into the emotion estimation-oriented database 87 the emotional state discriminated at S102 and the range of values of pen station information calculated at S103, the emotional state and the range of values of pen state information being associated with the acquired pen ID (S106).

The control circuit 81 then discriminates whether the predetermined times T1, T2, T3, T4, and T5 have ended regarding all the emotional states to be estimated (S107). If it is discriminated at S107 that the predetermined times have yet to be terminated, the control circuit 81 is given the brain wave data and the pen state information at the time of the user being in another emotional state in the next predetermined time. The control circuit 81 then returns control to S101 and repeats the subsequent steps.

If it is discriminated at S107 that the predetermined times T1, T2, T3, T4, and T5 have ended regarding all the emotional states to be estimated, the control circuit 81 generates or updates the range information regarding the ranges of general pen state information by performing, for example, the process of averaging the range information regarding each range of pen state information associated with each of the emotional states of numerous users stored in association with pen IDs in the emotion estimation-oriented database 87. The control circuit 81 stores into the emotion estimation-oriented database 87 the generated or updated range information regarding the ranges of general pen state information each in association with each of the "relaxed," "concentrated," "irritated," "distracted," and "angry" emotional states. The control circuit 81 then terminates the processing.

In the manner described above, the emotion estimation-oriented database 87 of the emotion server apparatus 8 stores the information associating the emotional states of each user identified by the pen ID with the range information regarding the ranges of pen state information. At the same time, the emotion estimation-oriented database 87 stores the range information regarding the ranges of general pen state information associated with the emotional states of general users not identified by pen IDs.

Thus when the user performs pointing input to the tablet terminal using the electronic pen, the pen state information regarding the electronic pen held by the current user may be used as reference information for searching through the emotion estimation-oriented database 87 of the emotion server apparatus 8. The search makes it possible to estimate the emotional state associated with the pen state information.

In this case, if the electronic pen held by the user has the same pen ID as that registered in the emotion estimation-oriented database 87, the information stored in the emotion estimation-oriented database 87 in association with the pen ID may be retrieved. The retrieval permits accurate estimation of the emotional state of the current user in accordance with the characteristics of electronic pen operations peculiar to the user identified by the pen ID. Also in this embodiment, the emotion estimation-oriented database 87 stores the range information regarding the ranges of general pen state information associated with each emotional state. The storage provides the advantage of allowing the general pen state information to be used to also estimate the emotional state of a user for whom the information associating the emotional states with the pen state information in accordance with the pen ID is not stored in the emotion estimation-oriented database 87.

<Second Example of the System for Building the Emotion Estimation-Oriented Database>

In the above-described first example of the system for building the database, the association processing device 4 is needed to associate the pen state information with the brain wave data as typical biological information for discriminating the emotional state. A second example of the system for building the database, to be discussed below, dispenses with the association processing device 4.

Figure 8:
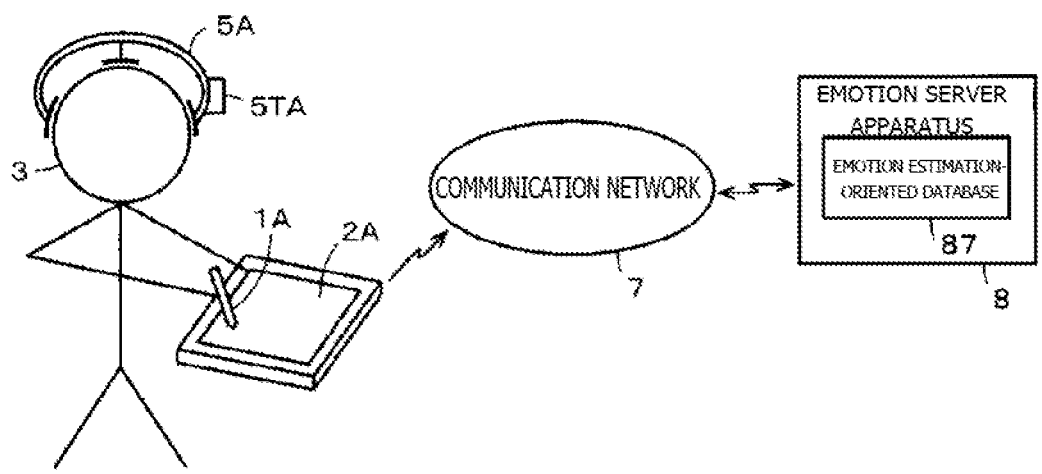
FIG. 8 is a schematic diagram explaining an outline of a building apparatus for building an emotion estimation-oriented information storage device as another embodiment of the present disclosure.

FIG. 8 explains an outline of the second example of the system for building the database. In this example, the user 3 may wear on the head a simple electroencephalograph 5A such as one disclosed in Patent Document 1. The simple electroencephalograph 5A includes a wireless communication circuit 5TA complying with a shortrange wireless communication protocol such as Bluetooth (registered trademark) in order to transmit wirelessly the brain wave data acquired from the user (called the simple brain wave data).

Also in this example, an electronic pen 1A includes a wireless communication means complying with the Bluetooth (registered trademark) protocol, not depicted in FIG. 8, in order to receive the simple brain wave data transmitted wirelessly from the simple electroencephalograph 5A. The electronic pen 1A outputs the simple brain wave data received from the simple electroencephalograph 5A to the position detection apparatus of a tablet terminal 2A as information added to the position detection signal.

Figure 9:
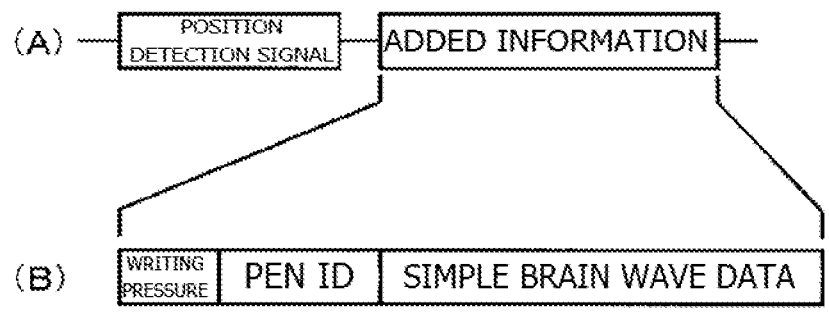
FIG. 9 is a schematic diagram explaining the building apparatus for building the emotion estimation-oriented information storage device as the other embodiment.

That is, as illustrated in Subfigure (A) in FIG. 9, the electronic pen 1A outputs the position detection signal and the added information repeatedly to the position detection apparatus of the tablet terminal 2A. For the electronic pen 1A of this example, the added information is made up of writing pressure information, a pen ID, and simple brain wave data as illustrated in Subfigure (B) in FIG. 9. As in the above-described first example, the electronic pen 1A outputs the added signal as a digital signal to the position detection apparatus of the tablet terminal 2A.

The tablet terminal 2A is configured the same as in the above-described first example. It is to be noted, however, that the tablet terminal 2A of the second example acquires not only the writing pressure and the pen ID but also the simple brain wave data as the added information and that the tablet terminal 2A has the function of transmitting the pen state information and the simple brain wave data associated with the pen ID to the emotion server apparatus 8 via the communication network 7, as will be discussed later.

[Typical Electronic Circuit Configurations of the Electronic Pen 1A and the Position Detection Apparatus 20A of the Tablet Terminal 2A]

Figure 10:
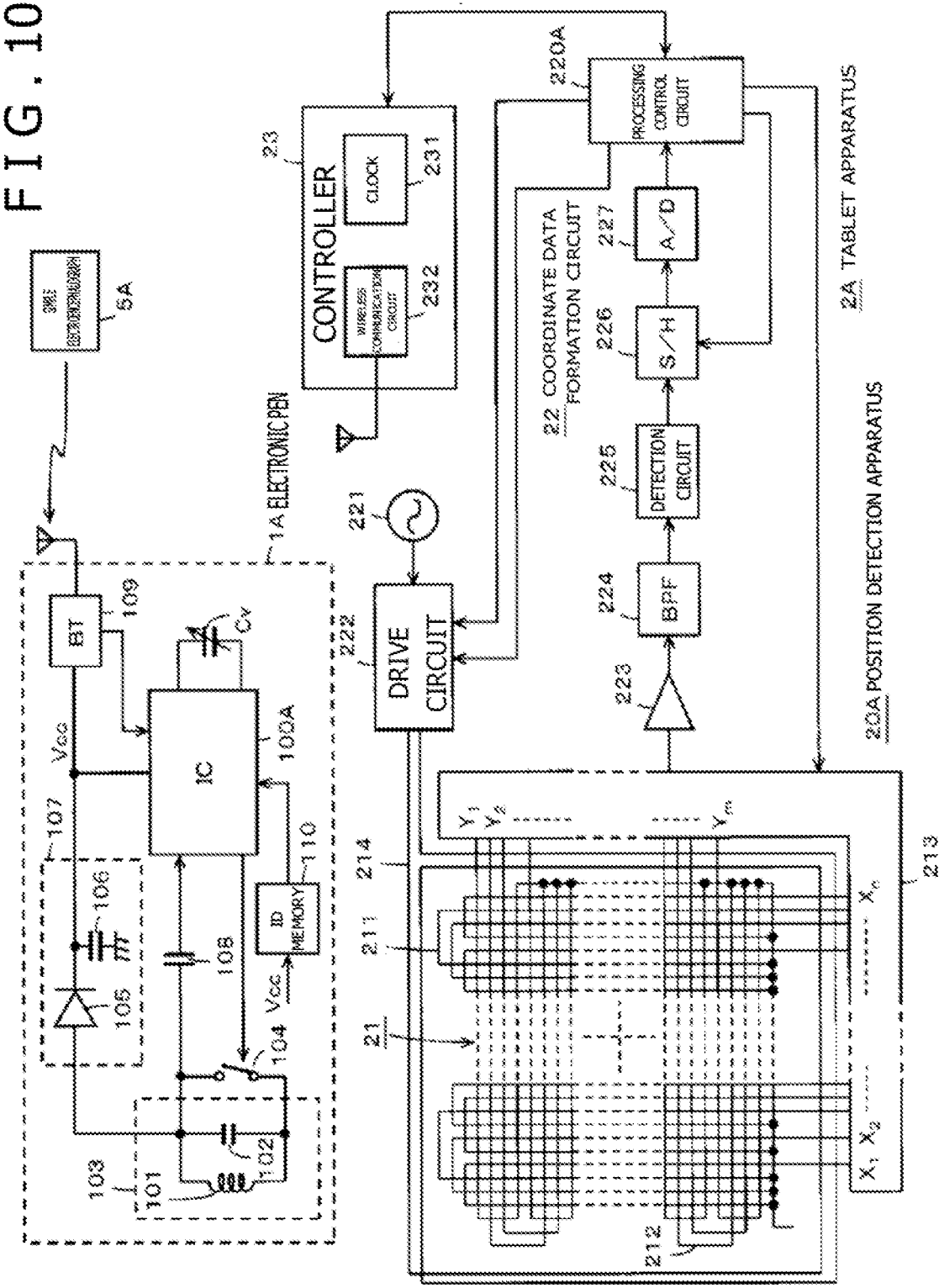
FIG. 10 is a schematic diagram depicting typical electric circuit configurations of an electronic pen and a tablet terminal making up the embodiment in FIG. 8.

FIG. 10 depicts an equivalent circuit of the electronic pen 1A and a typical circuit configuration of position detection apparatus 20A of the tablet terminal 2A in the second example. In FIG. 10, the same components as those of the electronic pen 1 and of the position detection apparatus 20 of the tablet terminal 2 in the first example in FIG. 2 are designated by the same reference numerals.

In the second example, as depicted in FIG. 10, the electronic pen 1A includes a wireless communication circuit 109 complying with the Bluetooth (registered trademark) protocol. The wireless communication circuit 109 is supplied with a power supply voltage Vcc from a rectifier circuit 107. The wireless communication circuit 109 supplies the received simple brain wave data to an IC 100A.

The IC 100A of the electronic pen 1A in this example generates added information (digital signal) formed by the simple brain wave data received by the wireless communication circuit 109, in addition to the writing pressure information detected from the capacitance of the variable capacitor Cv and the pen ID stored in an ID memory 110. As in the electronic pen 1 of the first example, the digital signal of the added information is used to place a switch circuit 104 under on-off control. The added information is output in the form of an ASK-modulated signal to the sensor 21 of a position 20A in the tablet terminal 2A. The other aspects of the configuration and the operation of the electronic pen 1A are the same as with the electronic pen 1 of the first example.

Just like the position detection apparatus 20 of the tablet terminal 2A in the first example, the position detection apparatus 20A of the tablet terminal 2A detects the position pointed by the electronic pen 1A as well as the height position and tilt of the electronic pen 1A on the basis of the position detection signal from the electronic pen 1A. Using the added information from the electronic pen 1A, the position detection apparatus 20A of the tablet terminal 2A detects the writing pressure information, the pen ID, and the simple brain wave data.

A processing control circuit 220A in the position detection apparatus 20A of the tablet terminal 2A then generates the pen state information formed by the information regarding the position pointed by the electronic pen 1A, writing pressure information, tilt information, and height position information. The processing control circuit 220A associates the pen state information with both the simple brain wave data and the pen ID before transmitting the mutually associated information to the controller 23. The controller 23 adds time information from the clock 231 as timestamp information to the information associating the pen state information with the simple brain wave data and pen ID following their receipt from the processing control circuit 220A. The controller 23 transmits the timestamp-supplemented information to the emotion server apparatus 8 through the wireless communication circuit 232 over the communication network 7.

Incidentally, the operations performed by the position detection apparatus 20A of the tablet terminal 2A to detect the position pointed by the electronic pen 1A, to detect the added information, and to detect the pen state information made up of the tilt and height position are exactly the same as those operations carried out by the position detection apparatus 20 of the tablet terminal 2 in the first embodiment.

In the second example, the emotion server apparatus 8 processes the information received from the tablet terminal 2A in the same manner as the information received from the association processing device 4 of the first example. In so doing, the emotion server apparatus 8 builds the emotion estimation-oriented database 87 such as that discussed above.

As described above, the second example dispenses with the association processing device 4. This provides the benefit of simplifying the configuration of the database building system.

Alternatively, the simple brain wave data sent wirelessly from the simple electroencephalograph 5A may be received not by the electronic pen 1A but by the tablet terminal 2A.

<Third Example of the System for Building the Database>

A third example of the system for building the database, to be explained hereunder, also dispenses with the association processing device 4 of the first example, as with the second example. In the third example, the emotional state of the electronic pen user is estimated not by use of brain wave data but by recourse to the technique of Patent Document 2 to measure biological information other than the user's brain waves, such as pulse rate and blood flow.

Figure 11:
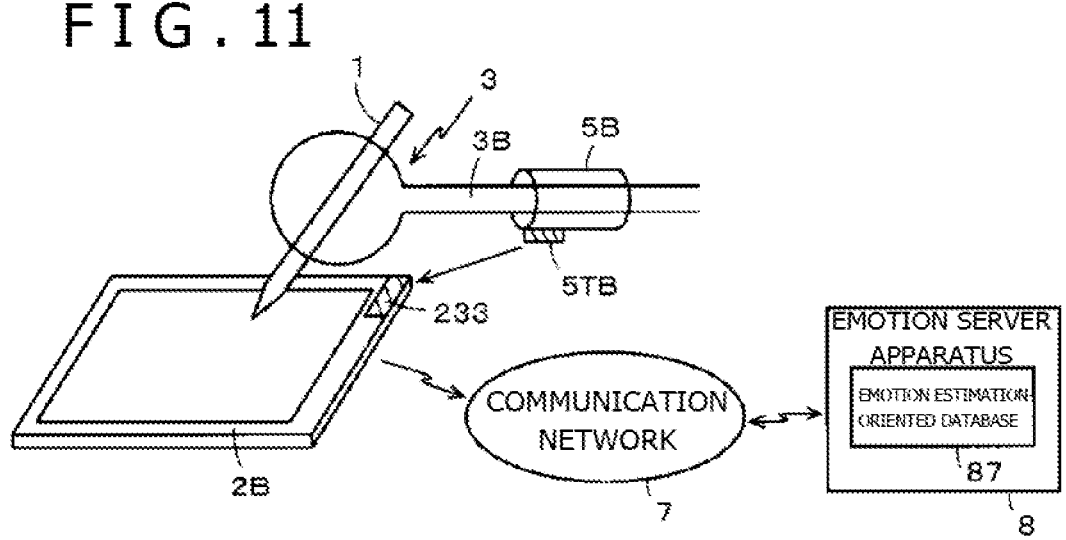
FIG. 11 is a schematic diagram explaining an outline of a building apparatus for building an emotion estimation-oriented information storage device as a further embodiment of the present disclosure.

FIG. 11 explains an outline of the third example of the system for building the database. In the third example, the user 3 holds the same electronic pen 1 as that in the first example. In the third example, the user 3 wears, typically on the arm 3B, a biological information detection apparatus 5B for detecting pulse rate and blood flow, the apparatus being disclosed in Patent Document 2, for example. The biological information detection apparatus 5B includes a wireless communication circuit 5TB complying with a short-range wireless communication protocol such as Bluetooth (registered trademark) in order to transmit wirelessly the detected data of biological information such as pulse rate and blood flow of the user 3.

A tablet terminal 2B of the third example includes a wireless communication circuit 233 complying with the Bluetooth (registered trademark) protocol in order to receive the detected data of biological information transmitted wirelessly from the biological information detection apparatus 5B. The tablet terminal 2B then associates the detected data of biological information received from the biological information detection apparatus 5B as well as the pen state information acquired as discussed above on the basis of signals from the electronic pen 1 with the pen ID obtained from the electronic pen 1. The tablet terminal 2B transmits the mutually associated information to the emotion server apparatus 8 via the communication network 7.

Figure 12:
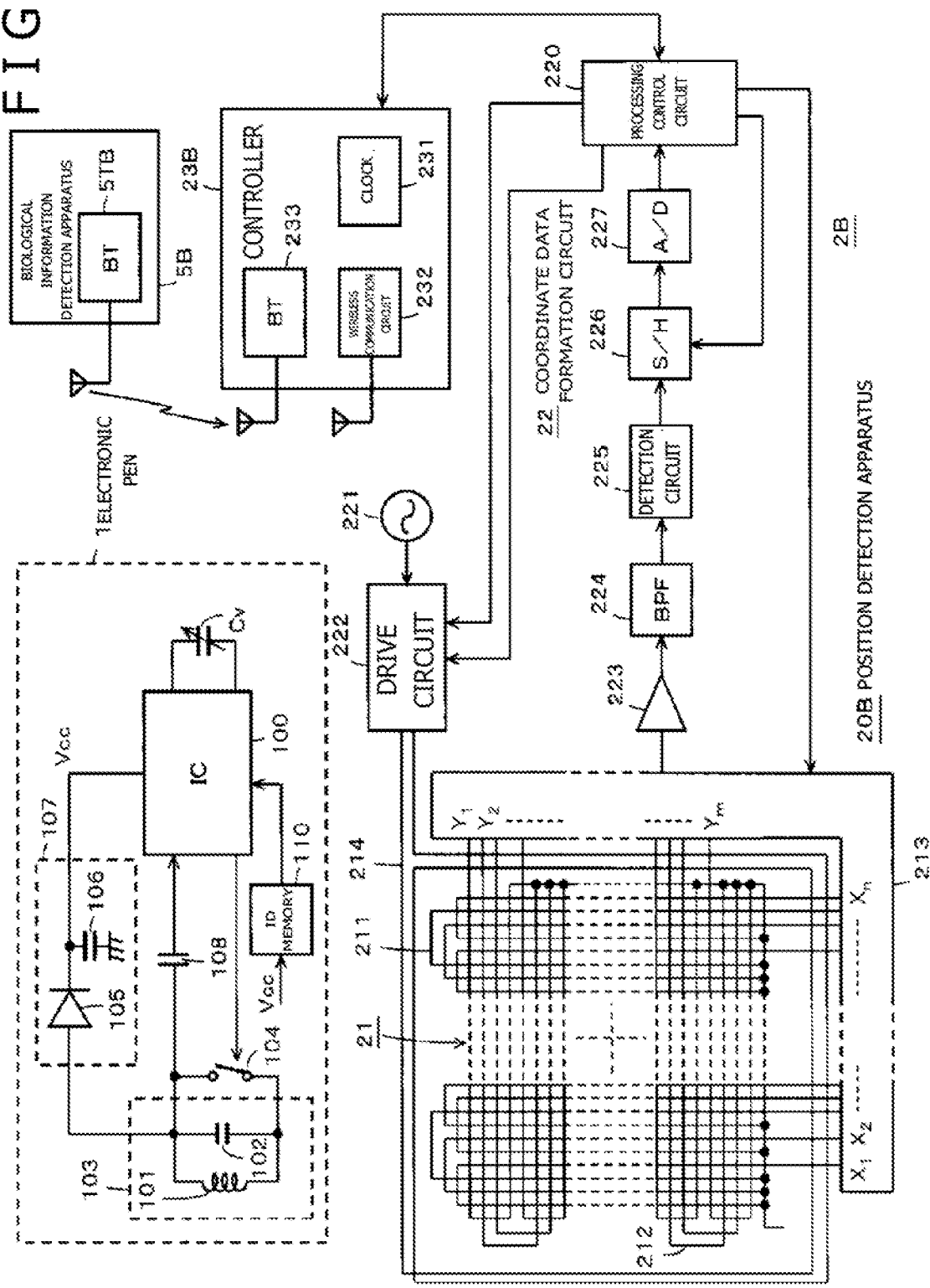
FIG. 12 is a schematic diagram depicting typical electric circuit configurations of an electronic pen and a tablet terminal making up the embodiment in FIG. 11.

Typical electronic circuit configurations of the electronic pen 1 and of the position detection apparatus 20B in the tablet terminal 2B FIG. 12 depicts an equivalent circuit of the electronic pen 1 and a typical circuit configuration of a position detection apparatus 20B of the tablet terminal 2B in the third example. In FIG. 12, the same components as those in the first example in FIG. 2 are designated by the same reference numerals.

As depicted in FIG. 12, the electronic pen 1 has substantially the same circuit configuration and performs substantially the same operations as the example in FIG. 2. Those components of the tablet terminal 2B which operate in conjunction with the electronic pen 1 are also configured and act substantially the same as the example in FIG. 2. The configuration of a controller 23B is different from that of the controller 23 in the example of FIG. 2.

That is, the controller 23B of the position detection apparatus 20B in the tablet terminal 2B includes the wireless communication circuit 233 that communicates with the wireless communication circuit 5TB included in the biological information detection apparatus 5B. The tablet terminal 2B allows the controller 23 to associate the pen state information coming from a processing control circuit 220B and related to the pen ID with detected data of biological information received by the wireless communication circuit 233. The tablet terminal 2B further causes the controller 23 to add time information from the clock 231 to the mutually associated information before transmitting the whole information to the emotion server apparatus 8 through the wireless communication circuit 232 over the communication network 7.

In the third example, the operations performed by the position detection apparatus 20B of the tablet terminal 2B to detect the position pointed by the electronic pen 1, to detect the added information, and to detect the pen state information made up of the tilt and height position are exactly the same as the operations carried out by the position detection apparatus 20 of the tablet terminal 2 in the first embodiment.

The third example thus dispenses with the association processing device 4. This provides the advantage of simplifying the configuration of the database building system and, with the tablet terminal 3B including a wireless communication circuit for communication with the biological information detection apparatus 5B, offers the benefit of simplifying the configuration of the electronic pen 1 as well.

With the above examples, it was explained that the biological information for discriminating a person's emotional states includes brain wave data, simple brain wave data, pulse rate, and blood flow. However, this is not limitative of the present disclosure. Alternatively, blinking, line-of-sight movement, and micro-vibration may be used singly or in combination with other biological information such as was discussed above in determining the person's emotional states.

It was also explained that the brain wave data is sent raw from the association processing device 4 to the emotion server apparatus 8 in the first example, that the simple brain wave data is sent raw to the server apparatus 8 through the tablet terminal 2A in the second example, that the biological information of pulse rate and blood flow is sent raw to the server apparatus 8 through the tablet terminal 2A in the third example, and that the raw data is used by the emotional state discrimination circuit 84 of the emotion server apparatus 8 in analyzing the user's emotional states. In this case, a large amount of data is sent to the emotion server apparatus 8, which can lower the transmission speed.

This situation may be bypassed by the association processing device 4 or by the tablet terminal 2A or 2B taking over the functional processing of the emotional state discrimination circuit 84 involving the analysis of brain wave data for emotional state discrimination. As another alternative, the processing may be carried out internally by the simple electroencephalograph 5A or by the biological information detection apparatus 5B. In this case, the association processing device 4, tablet terminal 2A or 2B, simple electroencephalograph 5A, or biological information detection apparatus 5B may add emotional state identification information to each of the discriminated emotional states. For example, the emotional state identification information S1 may be added to the "relaxed state," S2 to the "concentrated state," S3 to the "irritated state," S4 to the "distracted state," and S5 to the "angry state." Then the emotional state identification information may be associated with the pen state information when transmitted to the emotion server apparatus 8.

For example, as illustrated in FIG. 4, in a relaxed time period in which the emotional state is the "relaxed state," the pointed position information Crd1, writing pressure information Pr1, ID1 as the pen ID, tilt information SL1 (not depicted), and height information H1 (not depicted) making up the pen state information are associated with the emotional state identification information S1 about the "relaxed" emotional state before being transmitted altogether in a bundle to the server apparatus 8. This shortens the transmission time. The emotion server apparatus 8 may associate the emotional state identification information S1, S2, S3, S4 or S5 identifying the respective emotional states with the pen state information for storage into the emotion estimation-oriented database 87.

[Embodiment of the Emotion Estimation System]

Figure 13:
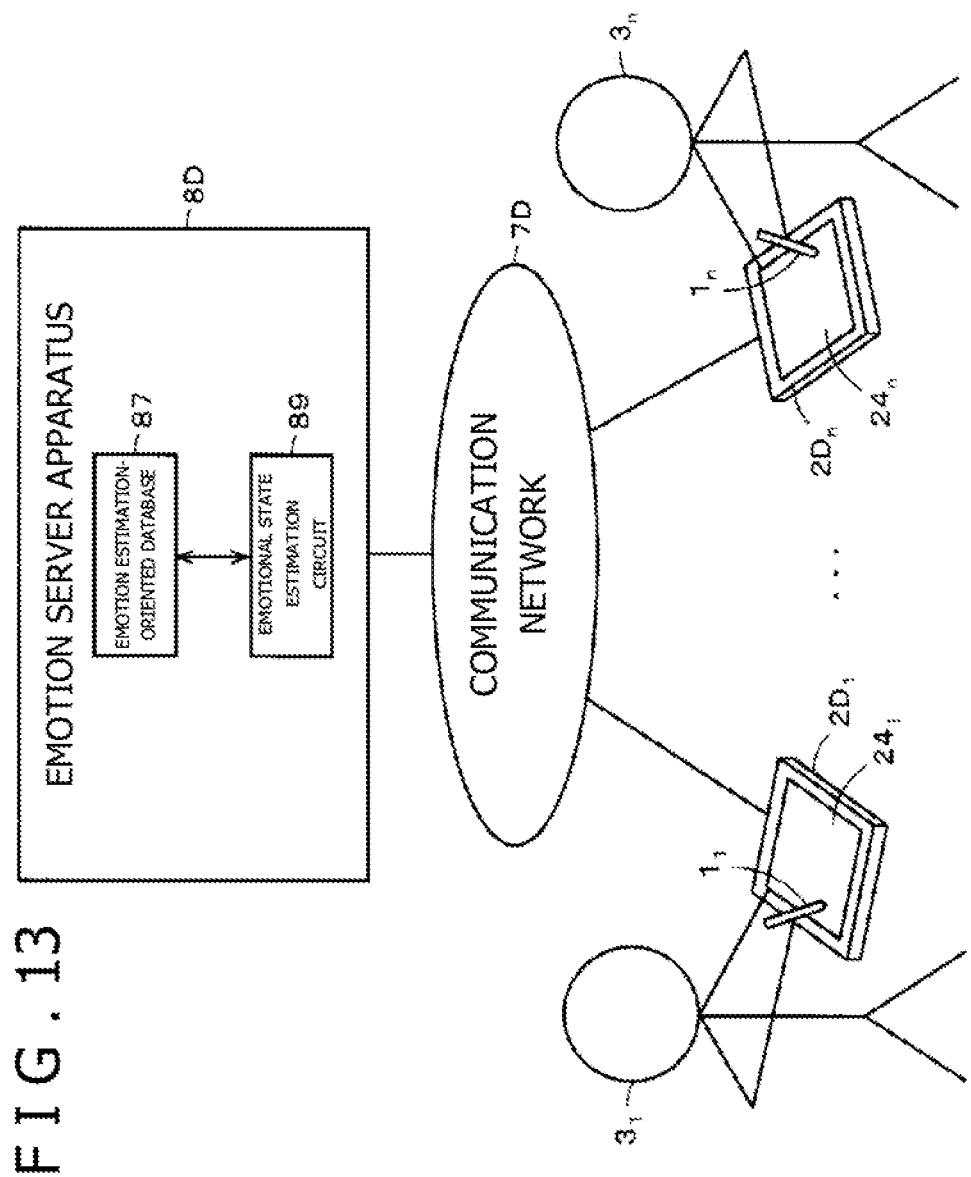
FIG. 13 is a schematic diagram explaining a typical overall configuration of a system that includes an emotion estimation apparatus as an even further embodiment of the present disclosure.

FIG. 13 explains an outline of a system for estimating the emotional state of the electronic pen user through the use of the emotion estimation-oriented database 87 built by the database building system described above.

In the emotion estimation system of this example, users $3_1, \ldots, 3_n$ (n is an integer of at least 1) possess their respective electronic pens $1_1, \ldots, 1_n$. Using their own electronic pens, the users perform character input and other types of input through tablet terminals $2D_1, \ldots, 2D_n$.

In this example, the electronic pens $1_1, \ldots, 1_n$ each have substantially the same configuration as that of the above-described electronic pen 1. The electronic pens $1_1, \ldots, 1_n$ are further configured to transmit the pen ID and the writing pressure information as information added to the position detection signal to each of the tablet terminals $2D_1, \ldots, 2D_n$. In this example, each of the electronic pens $1_1, \ldots, 1_n$ is paired with the corresponding one of the tablet terminals $2D_1, \ldots, 2D_n$ to constitute a coordinate input processing apparatus.

As with the above-described tablet terminal 2, the tablet terminals $2D_1, \ldots, 2D_n$ each include a position detection apparatus except that their controller is configured differently and that they have display devices $24_1, \ldots, 24_n$ each formed by a liquid crystal display (LCD). A display screen of each of the display devices $24_1, \ldots, 24_n$ is arranged to overlay the sensor on the position detection apparatus of each of the tablet terminals $2D_1, \ldots, 2D_n$. On the display screen, each of the users $3_1, \ldots, 3_n$ is allowed to perform pointing input using the corresponding one of the electronic pens $1_1, \ldots, 1_n$. That is, in this example, each of the tablet terminals $2D_1, \ldots, 2D_n$ has an electronic device configuration that includes an information processing apparatus in addition to the position detection apparatus.

Incidentally, each of the tablet terminals $2D_1, \ldots 2D_n$ may have two sections physically separated from or independent of one another and connected with each other in wired or wireless fashion, one of the two sections including the position detection apparatus configured the same as in the tablet terminal of the database building system, the other section including the information processing apparatus.

As with personal computers, the controller of each of the tablet terminals $2D_1, \ldots, 2D_n$ includes the function of a display control that generates images to be displayed on the display screen of each of the display devices $24_1, \ldots, 24_n$. That is, when each of the users $3_1, \ldots, 3_n$ performs pointing input using the corresponding one of the electronic pens $1_1, \ldots, 1_n$, the controller of the corresponding one of the tablet terminals $2D_1, \ldots, 2D_n$ displays images reflecting the pointing input on the display screen of the corresponding one of the display devices $24_1, \ldots, 24_n$.

In this example, upon receipt of the pointing input from each of the electronic pens $1_1, \ldots, 1_n$, the controller of the corresponding one of the tablet terminals $2D_1, \ldots, 2D_n$ generates an emotional state estimation request that includes the pen ID and the pen state information acquired from the corresponding electronic pen. The controller transmits the generated emotional state estimation request to an emotion server apparatus 8D via a communication network 7D. The emotion server apparatus 8D constitutes an emotion estimation apparatus.

The emotion server apparatus 8D includes the emotion estimation-oriented database 87 configured as described above and, as depicted in FIG. 15 to be discussed later, also includes an emotional state estimation circuit 89 and a providing information generation circuit 90. Upon receipt of an emotion state estimation request via the communication network 7D, the emotional state estimation circuit 89 searches through the emotion estimation-oriented database 87 to estimate a corresponding emotional state using the pen ID and the pen state information included in the request as the reference information. The providing information generation circuit 90 notifies the party that transmitted the emotion state estimation request of the estimated emotional state as needed, generates providing information associated with the estimated emotional state, and returns the generated providing information to the requesting party.

The communication network 7D may be configured with the Internet and public networks including mobile telephone networks, as with the above-described communication network 7. Alternatively, the communication network 7D may be a wireless LAN that uses Wi-Fi (registered trademark). As another alternative, the communication network 7D may be a wired LAN connecting the emotion server apparatus 8 with the association processing device 4 by wire.

[Typical Configuration of the Coordinate Input Processing Apparatus]

Figure 14:
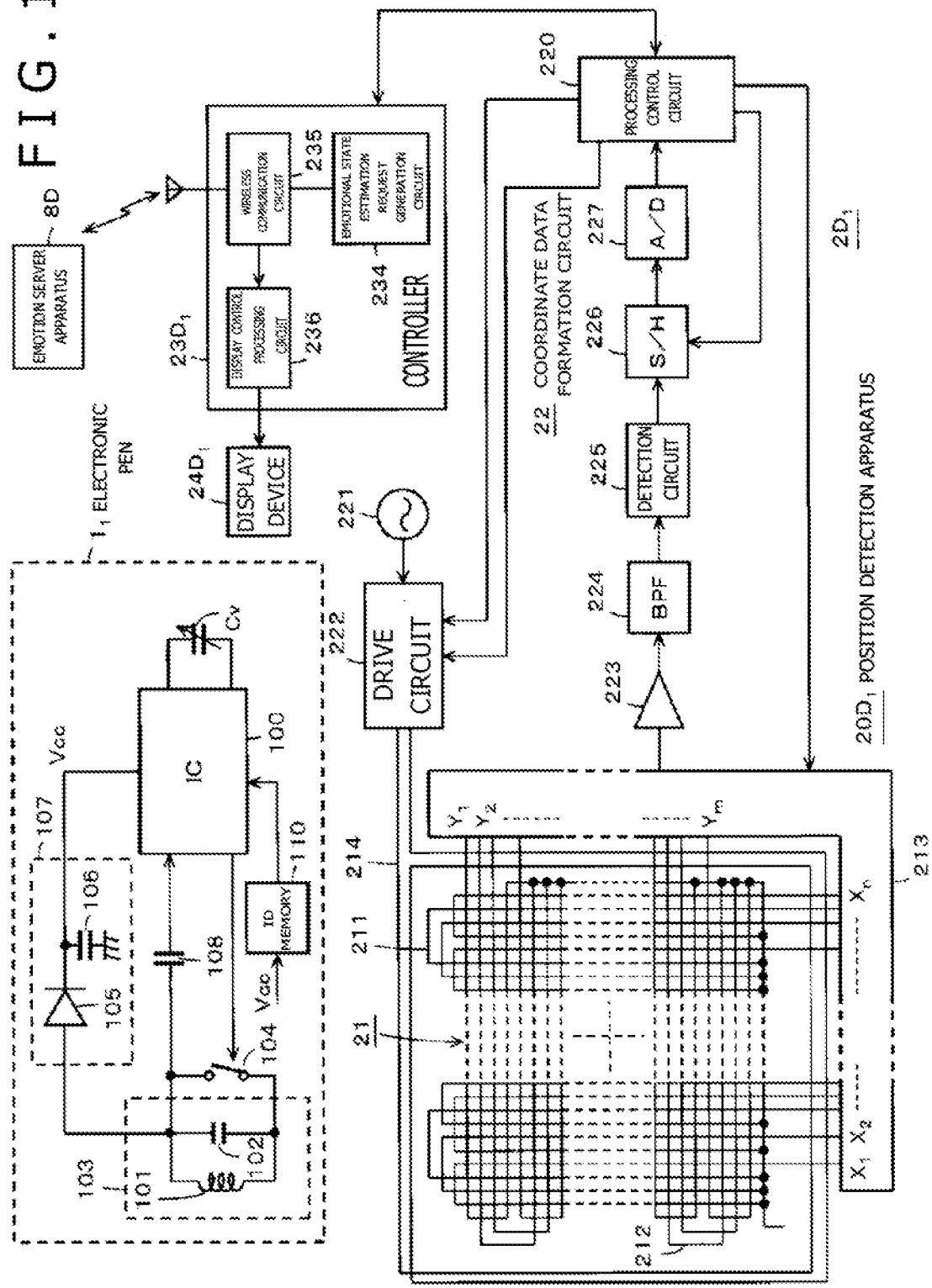
FIG. 14 is a schematic diagram depicting typical electric circuit configurations of an electronic pen and a tablet terminal making up the embodiment in FIG. 13.

FIG. 14 depicts a typical electronic circuit of a coordinate input processing apparatus of this embodiment. The apparatus corresponds to one of the pairs formed respectively between the electronic pens $1_1, \ldots, 1_n$ on the one hand and the tablet terminals $2D_1, \ldots, 2D_n$ on the other hand. The electronic pens $1_1, \ldots, 1_n$ have the same configuration, and the tablet terminals $2D_1, \ldots, 2D_n$ also have the same configuration. For this reason, FIG. 14 illustrates the electronic pen $1_1$ and the tablet terminal $2D_1$ as representative of both parts.

As depicted in FIG. 14, the electronic pen $1_1$ has the same configuration as that of the above-described electronic pen 1. A position detection apparatus $20D_1$ of the tablet terminal $2D_1$ has the same configuration as that of the above-described position detection apparatus 20 of the tablet terminal 2 except for the display device $24_1$ and a controller $23D_1$.

The controller $23D_1$ includes an emotional state estimation request generation circuit 234, a wireless communication circuit 235, and a display control circuit 236. When detecting that the user $3_1$ has performed pointing input to the tablet terminal $2D_1$ using the electronic pen $1_1$, the emotional state estimation request generation circuit 234 generates an emotional state estimation request that includes the pen ID and the pen state information received from the processing control circuit 220, and transmits the generated request to the emotional server apparatus 8D through the wireless communication circuit 235 over the communication network 7D.

On the basis of information from the processing control circuit 220 regarding the position pointed by the electronic pen $1_1$, the display control circuit 236 performs display control processing on a display image to be displayed on the screen of the display circuit $24_1$. Also, upon receipt of the provided information returned from the emotion server apparatus 8D via the wireless communication circuit 235 in response to the emotional state estimation request, the display control circuit 236 performs display control processing on the display image to be displayed on the screen of the display device $24_1$ in accordance with the provided information received.

[Typical Configuration of the Emotion Server Apparatus 8D]

Figure 15:
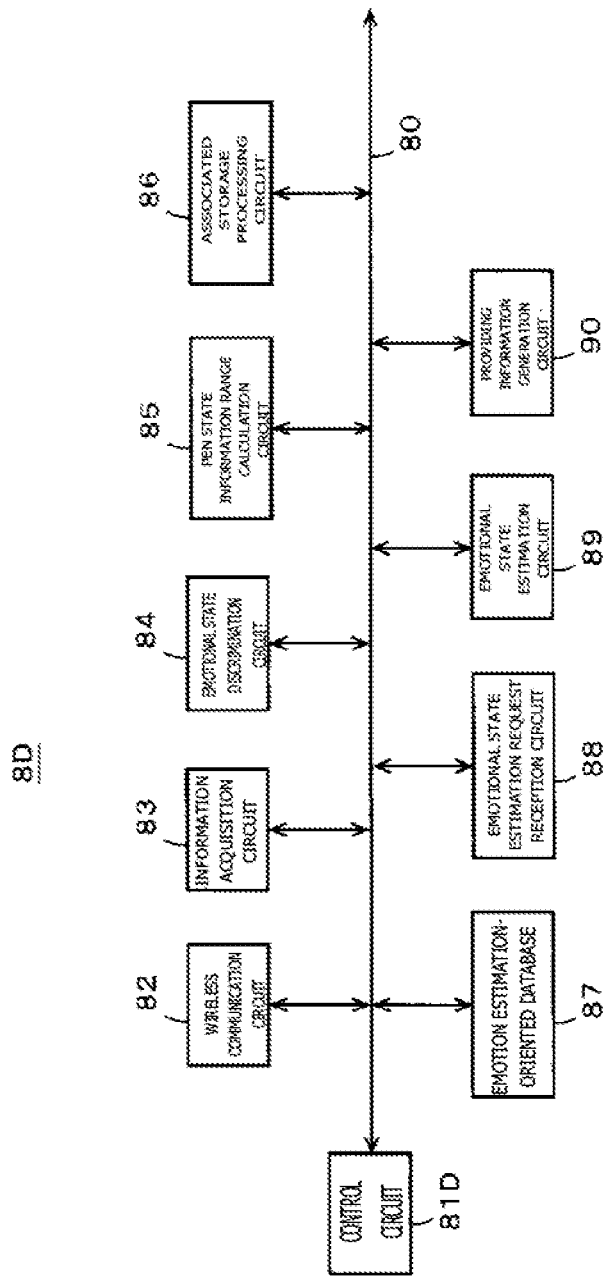
FIG. 15 is a block diagram depicting a typical configuration of the emotion server apparatus making up the embodiment in FIG. 13.

FIG. 15 is a block diagram depicting a typical hardware configuration of the emotion server apparatus 8D. The emotion server apparatus 8D of the example in FIG. 15 is an emotion estimation apparatus implemented by unmodified use, as an emotion estimation apparatus, of the emotion server apparatus 8 that includes the emotion estimation-oriented database 87 built by the above-described database building system. That is, a control circuit 81D is connected via system bus 80 with the wireless communication circuit 82, information acquisition circuit 83, emotional state discrimination circuit 84, pen state information range calculation circuit 85, associated storage processing circuit 86, and emotion estimation-oriented database 87, as well as with an emotional state estimation request reception circuit 88, with the emotional state estimation circuit 89, and with the providing information generation circuit 90.

That is, the portion that has the control circuit 81D connected via the system bus 80 with the wireless communication circuit 82, information acquisition circuit 83, emotional state discrimination circuit 84, pen state information range calculation circuit 85, associated storage processing circuit 86, and emotion estimation-oriented database 87 makes up the component corresponding to the database building system as discussed above. The portion that has the control circuit 81D connected via the system bus 80 with the wireless communication circuit 82, emotion estimation-oriented database 87, emotional state estimation request reception circuit 88, emotional state estimation circuit 89, and providing information generation circuit 90 makes up the component of the emotion estimation apparatus corresponding to the emotion estimation system.

The components corresponding to the database building system were discussed above. Explained below are the components of the emotion estimation apparatus corresponding to the emotion estimation system.

In the emotion server apparatus 8D, the wireless communication circuit 82 transfers the received emotional state estimation request to the emotional state estimation request reception circuit 88. The emotional state estimation request reception circuit 88 extracts the pen ID and the pen state information from the received emotional state estimation request, and transfers what is extracted to the emotional state estimation circuit 89. Using the received pen ID and pen state information, the emotional state estimation circuit 89 searches through the emotion estimation-oriented database 87 to estimate a corresponding emotional state. The emotional state estimation circuit 89 transfers the estimated emotional state to the providing information generation circuit 90.

The providing information generation circuit 90 generates providing information corresponding to the estimated emotional state received, and transmits the generated information to the party having made the emotional state estimation request through the wireless communication circuit 82. The providing information may include information for notification of the estimated emotional state or display information associated with the estimated emotional state.

Incidentally, the processes of the emotional state estimation request reception circuit 88, emotional state estimation circuit 89, and providing information generation circuit 90 may be carried out by the control circuit 81D executing programs stored in an internal memory as a software function.

[Flow of the Emotional State Estimation Request Process Performed by each of the Tablet Terminals $2D_1, \ldots, 2D_n$]

Figure 16:
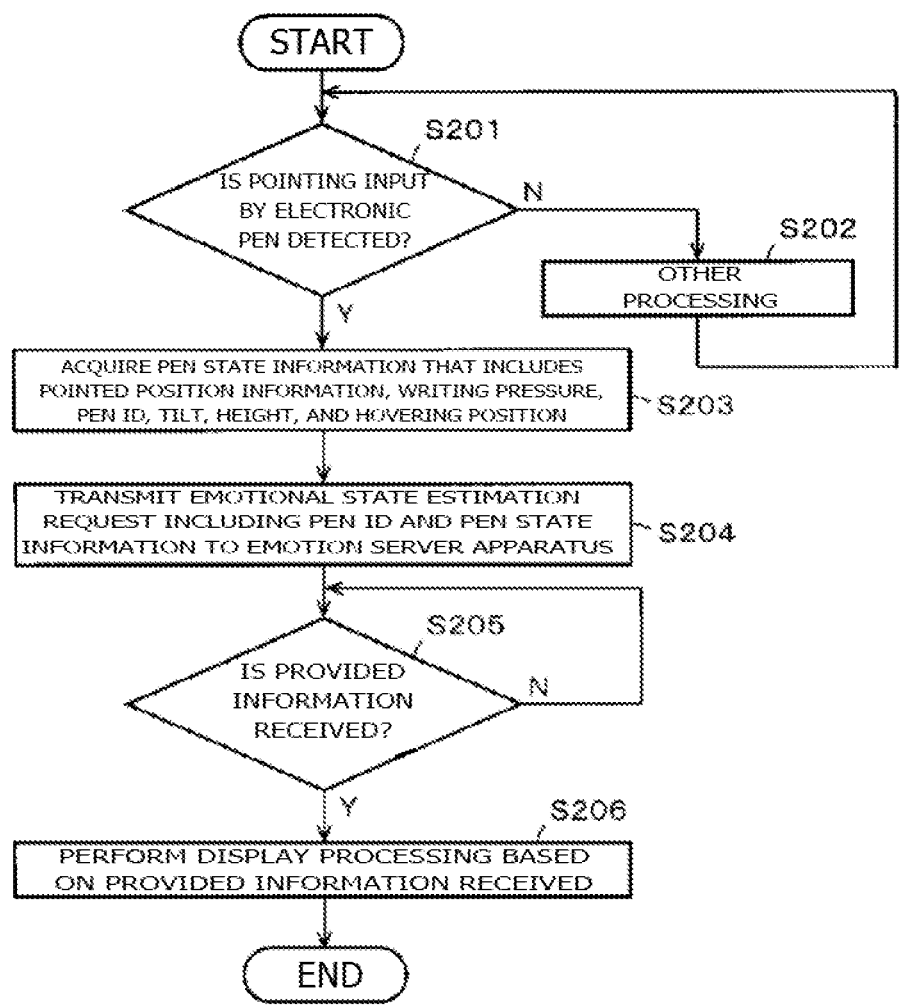
FIG. 16 is a flowchart explaining a typical flow of operational processing performed by the tablet terminal making up the embodiment in FIG. 13.

A typical flow of the emotional state estimation request process performed by each of the tablet terminals $2D_1, \ldots, 2D_n$ is explained below with reference to the flowchart in FIG. 16. It is assumed here that the controller $23D_1$ of the tablet terminal $2D_1$ makes the emotional state estimation request.

That is, the controller $23D_1$ monitors information from the processing control circuit 220 to discriminate whether pointing input by the electronic pen $1_1$ is detected (S201). When discriminating that the pointing input by the electronic pen $1_1$ is not detected at S201, the controller $23D_1$ performs other processing (S202). At the end of the processing, the controller $23D_1$ returns control to S201.

If it is discriminated at S201 that the pointing input by the electronic pen $1_1$ is detected, the controller $23D_1$ acquires from the processing control circuit 220 the pen state information including information regarding the position pointed by the electronic pen writing pressure, pen ID, tilt, height position, and hovering state position (S203).

The controller $23D_1$ then generates an emotional state estimation request that includes the acquired pen state information and pen ID, and transmits the generated request to the emotion server apparatus 8D (S204). Provided information is to be transmitted from the emotion server apparatus 8D in response to the emotional state estimation request. The controller $23D_1$ waits for receipt of the provided information (S205).

When receipt of the provided information from the emotion server apparatus 8D is verified at S205, the controller $23D_1$ performs processing based on the provided information received, i.e., carries out a display process in this example (S206).

[Flow of the Emotional State Estimation Process Performed by the Emotion Server Apparatus 8D]

Figure 17:
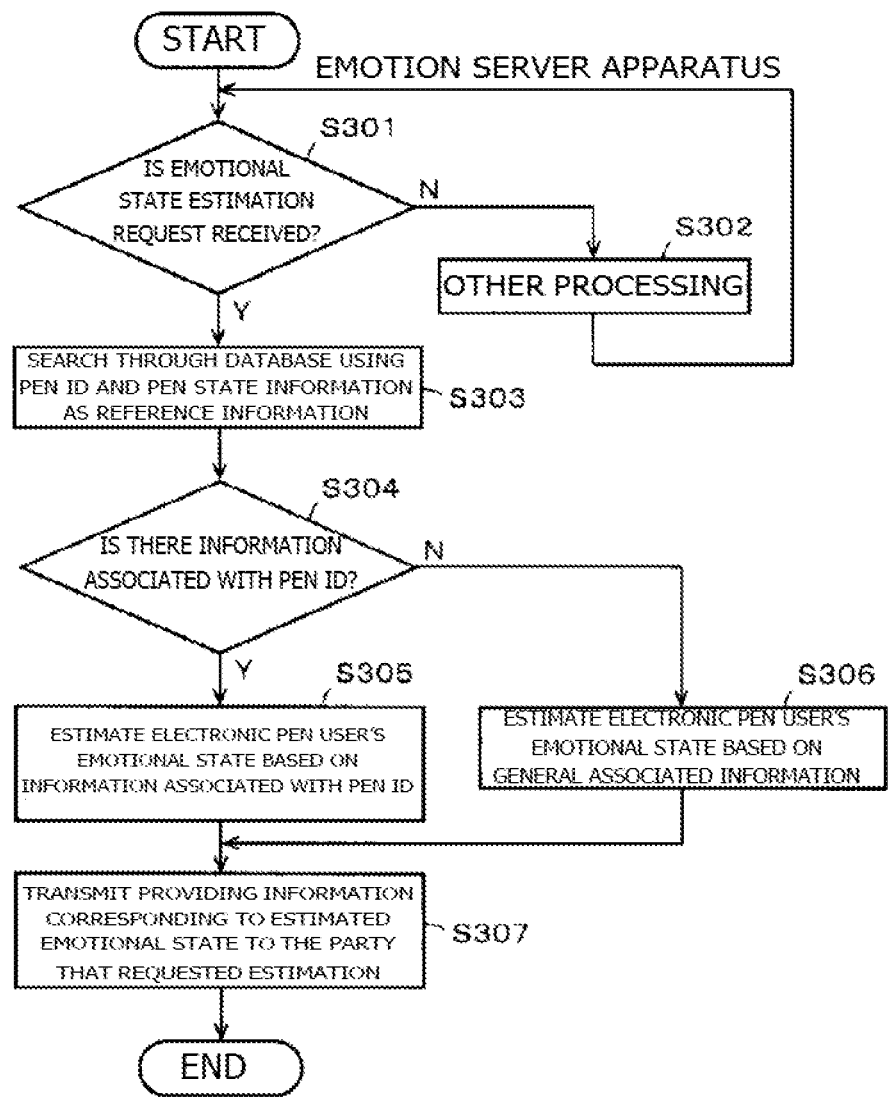
FIG. 17 is a flowchart explaining a typical flow of operational processing performed by the emotion server apparatus making up the embodiment in FIG. 13.

A typical flow of the emotional state estimation process performed by the emotion server apparatus 8D is explained below with reference to the flowchart of FIG. 17. It is assumed here that the control circuit 81D of the emotion server apparatus 8D is configured to provide a software-based processing function that executes the processes of the emotional state estimation request reception circuit 88, emotional state estimation circuit 89, and providing information generation circuit 90.

First, the control circuit 81D discriminates whether an emotional state estimation request is received (S301). If it is discriminated that the request is not received, the control circuit 81D performs other processing (S302). At the end of the processing, the control circuit 81D returns control S301.

If it is discriminated at S301 that the emotional state estimation request is received, the control circuit 81D searches through the emotion estimation-oriented database 87 using the pen ID and pen state information included in the request as the reference information (S303).

Next, the control circuit 81D discriminates whether the emotion estimation-oriented database 87 stores information associated with the pen ID included in the emotional state estimation request (S304). If it is discriminated at S304 that the information associated with the pen ID included in the emotional state estimation request is stored in the emotion estimation-oriented database 87, the control circuit 81D searches the database for an emotional state with the pen state information matching the information associated with the pen ID, and estimates the matching emotional state as the emotional state of the user having made the emotional state estimation request (S305). The control circuit 81D then generates providing information associated with the estimated emotional state, and transmits the generated providing information to the party that made the emotional state estimation request (S307).

Meanwhile, if it is discriminated at S304 that the information associated with the pen ID included in the emotional state estimation request is not stored in the emotion estimation-oriented database 87, the control circuit 81D searches the database for an emotional state with the pen state information matching the general associated information, and estimates the matching emotional state as the emotional state of the user having made the emotional state estimation request (S306). The control circuit 81D then generates providing information associated with the estimated emotional state, and transmits the generated information to the party that made the emotional state estimation request (S307).

The emotion estimation process performed by the emotion server apparatus 8D is then brought to an end.

[Display Process Associated with the Emotional State Estimated for the Tablet Terminal]

Suppose, for example, that the users $3_1, \ldots, 3_n$ are students making input for learning using the electronic pens $1_1, \ldots, 1_n$ in dealing with learning materials displayed on the display screens of the tablet terminals $2D_1, \ldots, 2D_n$, respectively.

Figure 18:
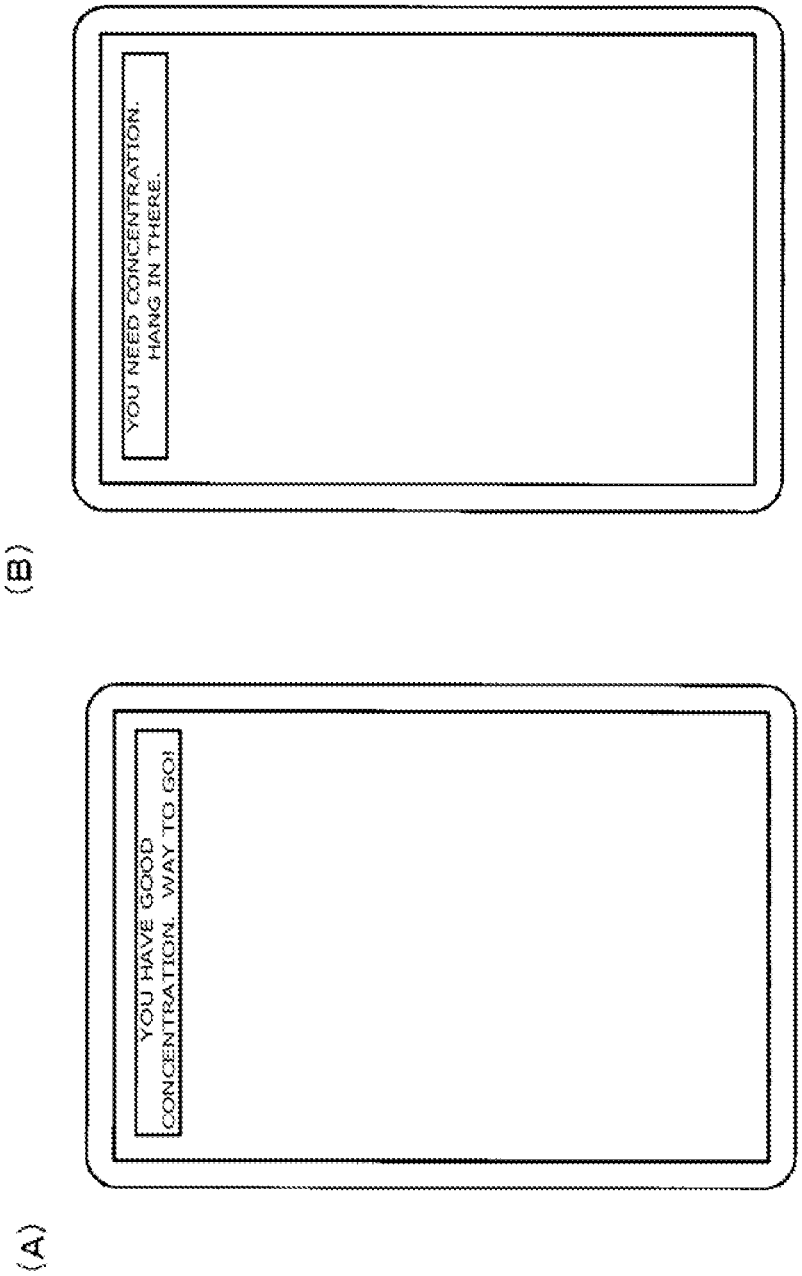
FIG. 18 is a schematic diagram explaining the embodiment in FIG. 13.

In this case, where the emotional state estimated by the emotion server apparatus 8D is the "concentrated state," for example, the emotion server apparatus 8D may provide character information such as "You have good concentration. Way to go!" as the providing information illustrated in Subfigure (A) in FIG. 18. Where the emotional state estimated by the emotion server apparatus 8D is the "distracted state" or "irritated state," for example, the emotion server apparatus 8D may provide character information such as "You need concentration". Hang in there" depicted in Subfigure (B) in FIG. 18. The character information serves as a pep talk with respect to the emotional state of the student, and thereby boosts the student's learning effectiveness.

As another example, in addition to displaying the emotional state of the electronic pen user in real time, the pen state information obtained from the electronic pen may be recorded for subsequent understanding of the emotional state of the user at the time of using the electronic pen. For example, if the pen state information is attached to a handwritten message sent to a relative, the relative who opens the message can receive the sender's emotion (e.g., gratitude) at the time the message was written along with the handwritten message. That is, not only the handwritten characters but also the emotion may be transmitted. The handwritten messages include a thank-you letter and a testament, among others.

Moreover, because the user's emotional state is estimated from the pen state information, the authenticity of documents such as a contract may be discriminated using the emotional state estimated from the pen state information regarding the signer who signed on the signature line, for example.

It was explained in connection with the embodiments above that the database building system and the emotion estimation system are separate entities. However, as discussed above, the emotion server apparatus 8D is configured to support both systems as depicted in FIG. 15. Thus the emotion server apparatus 8D may serve as a single system that includes both the database building system and the emotion estimation system described above. In the single system, the emotion server apparatus 8D may switch between the operations of the database building system and those of the emotion estimation system.

Specifically, where it is discriminated that the information transmitted from the association processing device 4 or from the tablet terminal 2A or 2B includes biological information such as brain wave data, simple brain wave data, pulse rate, or blood flow or the emotional state identification information S1 to S5, the emotion server apparatus 8D operates as the database building system.

On the other hand, where it is discriminated that the information transmitted from the association processing device 4 or from the tablet terminal 2A or 2B to the emotion server apparatus 8D does not include biological information such as brain wave data, simple brain wave data, pulse rate, or blood flow or the emotional state identification information S1 to S5, the emotion server apparatus 8D operates as the emotion estimation system. In this case, the emotion server apparatus 8D performs the process of estimating the user's emotion based on the pen state information and of providing the user with information regarding the estimated emotional state, for example.

Alternatively, information such as a flag specifying the use either as the database building system or as the emotion estimation system may be included in the signal transmitted from the association processing device 4, the tablet terminal 2A or 2B to the emotion server apparatus 8D. In this case, there is no need for the emotion server apparatus 8D to detect whether the biological information such as brain wave data, simple brain wave data, pule rate, or blood flow or the emotional state identification information S1 to S5 is included in the signal transmitted from the tablet terminal 2A or 2B to the server apparatus. Detection of the flag information need only be carried out for discrimination purposes.

Variations of the Above Embodiments

The pen state information is not limited to what was discussed above in conjunction with the examples. For example, sensors may be mounted on the grip portion of the electronic pen to detect the position held by the user and the strength with which the pen is gripped. The pen holding position and the pen gripping strength thus detected may be used as the pen state information. As another example, a sensor (sweat sensor) may be mounted on the grip portion of the pen to detect the user's sweating rate reflecting his or her psychological state. The detected sweating rate may then be used as the pen state information.

It was explained in connection with the examples above that the database is built using the biological information and the pen state information in association with one another, the biological information including brain wave data, simple brain wave data, pulse rate or blood flow, the two types of information being transmitted from the association processing device 4 or from the tablet terminal 2A or 2B to the emotion server apparatus 8 via the communication network 7. Alternatively, the emotion server 8 may be included in the association processing device 4 or in the tablet terminal 2. That is, the database may be built inside the association processing device 4 or in the tablet terminal 2A or 2B. This allows the process of emotion estimation to be alleviated by an amount reflecting the absence of data transmission through the communication network.

It was also explained in connection with the embodiments above that the pen ID identifying the electronic pen used by the user is stored in the emotional state-oriented database as the identification information identifying the user. However, if the user makes exclusive use of the tablet terminal as his or her own, the pen ID may be replaced with identification information (terminal ID) identifying both the tablet terminal and the user. In the case where the tablet terminal constitutes the coordinate input processing apparatus, the terminal ID of the tablet terminal also serves as a device ID identifying the coordinate input processing apparatus.

In such cases, the tablet terminal or the coordinate input processing apparatus may have its terminal ID or device ID stored in the storage device. In the database building system, the terminal ID or the device ID thus stored is associated with the biological information and pen state information for emotional state discrimination when transmitted to the emotion server apparatus. The terminal ID or the device ID is stored into the emotion estimation database in association with the emotional states resulting from the discrimination process and with the range information regarding the range of pen state information.

In the case of the emotion estimation system, the coordinate input processing apparatus places its device ID or the terminal ID stored in the storage device of the tablet terminal into the emotional state estimation request before transmitting the request to the emotion server apparatus.

Alternatively, the coordinate input processing apparatus may be configured using the tablet terminal including the position detection apparatus and an information processing apparatus including a computer furnished with a display. In this case, the device ID may be used as the identification information identifying the information processing apparatus.

It was also explained in connection with the embodiments above that the electronic pen and the tablet terminal operate by electromagnetic induction coupling technology. Alternatively, the electronic pen and the tablet terminal operating by the capacitive coupling method may be used as well.

Although it was explained above that the writing pressure is detected using the capacitance of a variable capacitor, the writing pressure may alternatively be detected using changes in inductance in a suitable configuration.

Other Embodiments or Variations

<Formats of Signals Transmitted from the Association Processing Device 4 or from the Tablet Terminal 2A or 2B to the Emotion Server Apparatus 8 or 8D>

Figure 19:
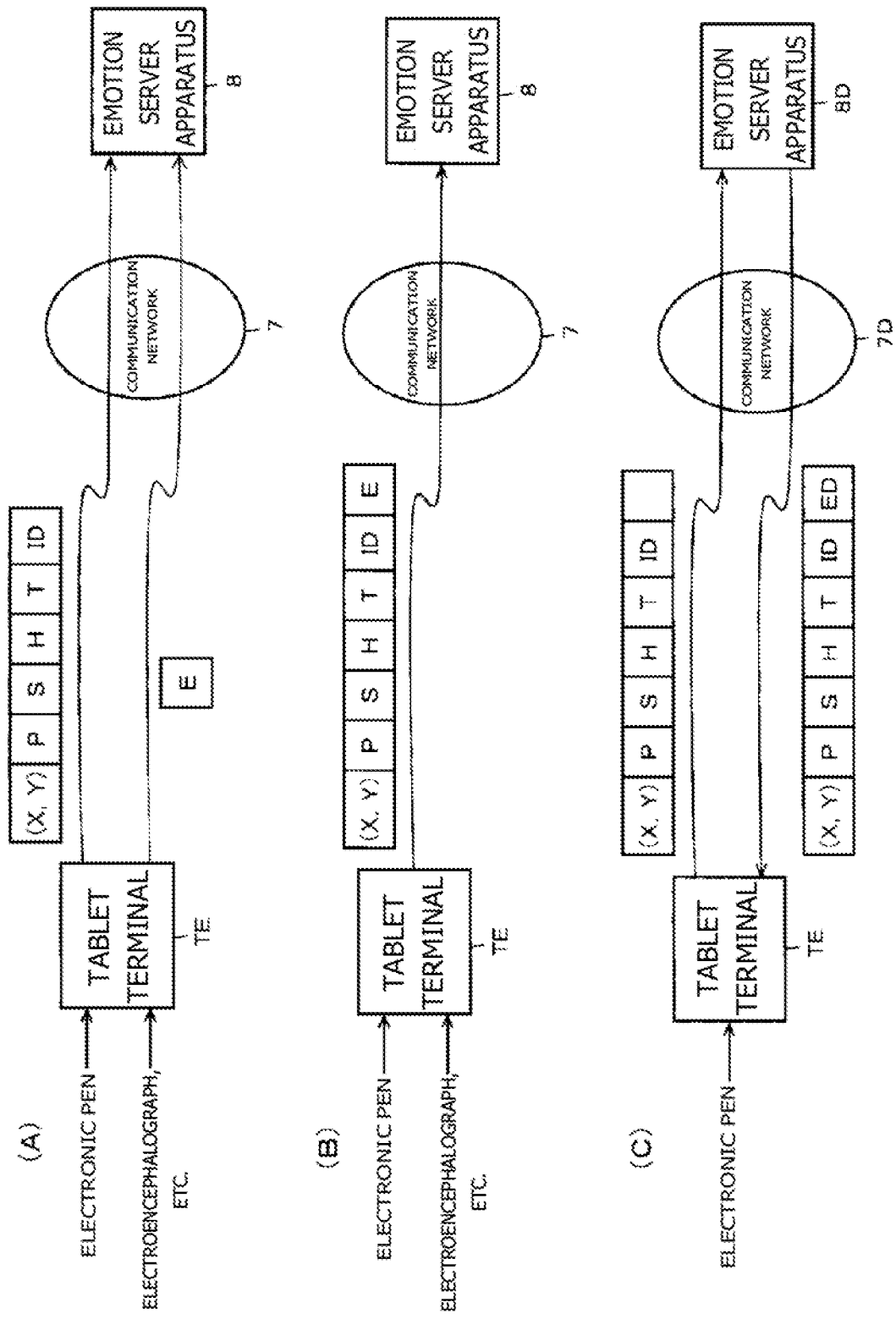
FIG. 19 is a schematic diagram explaining typical signal formats used by the building apparatus for building the emotion estimation-oriented information storage device, by the emotion estimation apparatus, and by an emotion estimation system as the embodiments of the present disclosure.

Explained below with reference to FIG. 19 are some typical formats of signals transmitted from the association processing device 4 or from the tablet terminal 2A or 2B to the emotion server apparatus 8 or 8D. It is assumed for the subsequent explanation that the function of the association processing device 4 is included in a tablet terminal TE.

In the examples of FIG. 19, the tablet terminal TE detects as the electronic pen-related information the coordinate data (X, Y) of the pointed position, writing pressure data P, tilt data S, and height position data H making up the pen state information, as well as the pen ID from the position detection signal and added information from the electronic pen. From the electroencephalograph or like equipment, biological information E such as brain wave data for discriminating a person's emotional state is input to the tablet terminal TE. In these examples, the pen ID is added so that the pen state information is stored for each electronic pen user in a database configured to permit acquisition of the relations between each electronic pen user and his or her emotional states. The pen ID need not be included in the signal format in the case where what needs to be obtained is not the relations between the pen state information and the emotional states of each electronic pen user but the relations between the general pen state information and the emotional states of all pen users.

In the example of Subfigure (A) in FIG. 19, the tablet terminal TE transmits the electronic pen-related information and biological information E for emotional state discrimination in separate signals to the emotion server apparatus 8 via the communication network 7. However, the emotion server apparatus 8 stores in its memory the simultaneously transmitted electronic pen-related information and biological information E for emotional state discrimination in association with each other. In this case, as depicted in Subfigure (A) in FIG. 19, the electronic pen-related information is transmitted repeatedly to the emotion server apparatus 8 in a signal format in which the coordinate data (X, Y) of the pointed position, writing pressure data P, tilt data S, height position data H, time (at which coordinates were input) T, and pen ID are arranged in that order, for example.

Next, in the example of Subfigure (B) in FIG. 19, the tablet terminal TE transmits repeatedly to the emotion server apparatus 8 the electronic pen-related information and the biological information E for emotional state discrimination in a single signal format. In this case, as depicted in Subfigure (B) in FIG. 19, the coordinate data (X, Y) of the pointed position, writing pressure data P, tilt data S, height position data H, time T, pen ID, and biological information E are arranged, in that order, for example, in the format of the signal transmitted repeatedly to the emotion server apparatus 8.

The example in Subfigure (C) in FIG. 19 addresses a case of the embodiment of the above-described emotion estimation system. Given in this case is a typical format of the signal in which the tablet terminal TE transmits the pen state information to the emotion server apparatus 8D and in which the emotion server apparatus 8D returns information indicative of the emotional states estimated with regard to the pen state information from the tablet terminal TE (the returned information indicates the relaxed, concentrated, irritated, distracted, or angry state).

In the case above, as illustrated in Subfigure (C) in FIG. 19, the tablet terminal TE transmits the signal in a format in which the coordinate data (X, Y) of the pointed position, writing pressure data P, tilt data S, height position data H, time T, and pen ID are arranged, in that order, for example, as the electronic pen-related information followed by an empty space (empty area or empty field) for accommodating the information ED indicative of the emotional state. In the example of Subfigure (C) in FIG. 19, the signal in this format is transmitted repeatedly to the emotion server apparatus 8D via the communication network 7.

In place of the empty space for the information ED indicative of the emotional state, there may be included either meaningless data such as all zeros as the information ED indicative of the emotional state or information representative of the emotional state estimation request. Alternatively, even if an explicit emotional state estimation request is not included in the empty space, upon receipt of a signal in a format that includes the empty space for the information ED indicative of the emotional state or a signal in a format that includes meaningless data such as all zeros as the information ED indicative of the emotional state, the emotion server apparatus 8D may discriminate that signal as one accompanied by the emotional state estimation request.

When returning information to the tablet terminal TE, the emotion server apparatus 8D inserts the information ED indicative of the emotional state estimated from the pen state information into the empty space of the format of the transmitted signal, as depicted in Subfigure (C) in FIG. 19. The returned information thus includes both the pen state information and the information ED indicative of the emotional state estimated from the pen state information in a single signal format. That is, it is known that the pen state information included in the signal format was written in the emotional state indicated by the information ED for emotional state indication. Thus adopting the signal format depicted in Subfigure (C) in FIG. 19 provides the benefit of the pen state information being transmitted or retained together with the information ED indicative of the emotional state in which the pen state information was written, thereby permitting multipurpose use of the pen state information.

<Another Embodiment of the Emotion Estimation System: An Example that Uses Artificial Intelligence>

Recent years have witnessed the burgeoning of massive data being processed (through machine learning) using neural networks called artificial intelligence (AI). Techniques have been devised to derive regularity from large amounts of data.

Machine learning is one mechanism of neural networks. There are two kinds of machine learning: supervised learning and unsupervised learning. Supervised learning has a "question-answer" format characterized by "learning of the relation between input and output" and "prediction of output from input."

Supervised machine learning is a method used where there exist large amounts of input data from which large amounts of output data are derived and where there are multiple layers (layer, characteristic extraction layer, hidden layer) of paths along which the output is derived from the input data, the input data being divided and integrated by characteristic in each of the layers, the input data being further weighted while subjected to feedback even as their weights are dynamically changed little by little in order to approach the output data. Recalculation of data with their weights dynamically changed little by little has been made possible by faster calculation processing in recent years, which has enabled machine learning.

The emotion server apparatus of the emotion estimation system in this embodiment performs the above-described machine learning on the information stored in the emotion estimation-oriented database. From the pen state information regarding a person who writes with the electronic pen, the emotion server apparatus thus generates trained data for estimating the emotional state of that person. Using the trained data, the emotion server apparatus estimates, from the pen state information regarding the person who writes with the electronic pen, the emotional state of that person at the time of writing.

That is, the emotion server apparatus of this embodiment acquires various characteristic amounts (coordinates, pressure, tilt, height, etc.) making up the pen state information as the information about the handwriting (called the handwriting data hereunder) of the person who wrote with the electronic pen. At this time, the person's emotions are estimated from the biological information intended for emotional state estimation such as brain wave data from a brain wave data detection apparatus. The information regarding the relations between the characteristic amounts of handwriting data (coordinates, pressure, tilt, height, etc.) on the one hand and the estimated emotions on the other hand is then accumulated in large quantities in a database. In this case, the characteristic amounts of handwriting data (coordinates, pressure, tilt, height, etc.) manifests a specific distribution with regard to each emotional state. Thus the database permits acquisition of the distribution of the characteristic amounts of handwriting data applicable to each emotional state. When the characteristic amounts of handwriting data at the time of writing with the electronic pen are determined to fall within the distribution of the characteristic amounts associated with a specific emotional state, the determination permits estimation of the emotional state of the person at the time of writing with the electronic pen.

With this embodiment, large quantities of data are analyzed by machine learning with new techniques in order to put into a matrix (tensor, trained data; see the matrix in FIG. 20) the relations between input data (characteristic amounts of handwriting data) and output data (emotions). This permits instantaneous deriving of the output data (emotions) from the input data (characteristic amounts of handwriting data), which contributes significantly to implementing faster processing. By establishing trained data, this embodiment allows emotions to be derived from handwriting data through calculations on a small scale.

The handwriting data has numerous characteristic amounts. Specifically, as described above, the data includes the coordinates (X, Y) of the position pointed by the electronic pen, writing pressure, height, tilt, writing speed, and their variations (differential values). What is important is which characteristic amounts are to be input to bring out an optimum emotion in carrying out efficient machine learning.

Multiple characteristic amounts are derived from the handwriting data associated with a specific emotion. Although it is possible to derive the emotion from the trained data derived from one specific characteristic amount, the estimation of emotion with higher accuracy is made possible by combining the trained data from the learning based on multiple characteristic amounts.

The operators for obtaining trained data are constituted by neural networks. They make up an input layer serving as the input and an output layer as the output, with multiple layers (characteristic extraction layers) interposed therebetween. The input data is divided into multiple items that are fitted to the elements of each layer (characteristic extraction layer). The fitting is accomplished by each of the elements being weighted in each layer. The weights of the elements in the respective layers are put into a matrix that constitutes a weight matrix (tensor, trained model). The weight matrix is allowed to be updated.

Below is an explanation of how machine learning is carried out.

<Preliminary Step>
(Building of a Database)

The characteristic amounts of handwriting data such as data about the coordinates (X, Y) of the pointed position, pressure, height, tilt, and time are received from the tablet terminal. From the electroencephalograph or like equipment, the data about the emotional states categorized on the basis of brain wave data is received. The handwriting data and the emotional state data are associated with one another and stored in the database. The emotional state data in this case may include, besides the measurement data from the electroencephalograph, categorized types of emotions (e.g., "anger," "delight") derived from the measurement data.

<First Step>
(Preparation of Learning Data Sets)

On the basis of the handwriting data stored in the database, learning data sets are prepared for each item of the handwriting data. The learning data sets include the coordinates (X, Y) of the pointed position, pressure, height, and tilt making up the pen state information, as well as variations (differential values) calculated from these values, and the writing speed and its variations calculated from the time T and from the pointed position coordinates (X, Y).

<Second Step>
(Preparation of the Trained Model: 1)

From the prepared learning data sets, specific handwriting data is selected, and specific characteristic amounts are also selected. The selected data is suitably divided before being set to the input layer of the operators. The types of the emotional states based on the specific handwriting data above are set to the output layer of the operators.

For example, from the specific handwriting data ("あ"), a specific characteristic amount (coordinates X, Y) is selected as the input data. The selected input data is divided as described above before being set to the input layer. The emotional state set to the same output layer as that of the emotional state associated with the specific handwriting data above is set as "true" or "hit."

<Third Step>
(Preparation of the Trained Model: 2)

The operators are used to vary the weight of each of the elements in order to approach the emotional state as the output data associated with the handwriting data constituting the input data. The weights are arranged into a weight matrix (tensor) that is updated every time a weight is varied.

<Fourth Step>
(Preparation of the Trained Model: 3)

Large quantities of handwriting data and biological information data regarding the emotional states are input to create the most appropriate weight matrix (tensor) satisfied by all data. This completes the trained data regarding each of the characteristic amounts of the handwriting data associated with each of the emotional states.

<Fifth Step>
(Utilization of the Trained Model)

When the characteristic amounts of newly generated handwriting data are transmitted from the tablet terminal to the emotion server apparatus together with an emotion estimation request, the emotion server apparatus estimates the emotional state associated with the characteristic amounts of handwriting data of which the distribution encompasses the characteristic amounts of the newly generated handwriting data, the estimation being made on the basis of the trained data for each of the characteristic amounts of the handwriting data generated as described above.

For example, if the handwriting data regarding the electronic pen is supplied to the emotion server apparatus in the signal format depicted in Subfigure (C) in FIG. 19, the emotion server apparatus estimates the emotional state associated with the characteristic amounts of the incoming handwriting data by use of the trained data about each of the characteristic amounts generated as discussed above. The emotion server apparatus then generates a signal ED of return information indicative of the estimated emotional state as depicted in Subfigure (C) in FIG. 19, and returns the signal ED to the tablet terminal.

In this case, the emotion server apparatus need not examine the distribution of the handwriting data from the tablet terminal TE with regard to the emotion estimation request. Instead, the emotion server apparatus may use the trained data about each of the characteristic amounts of the handwriting data so as to obtain the emotional state as the output data. It is thus possible to derive the emotional state from the handwriting data through calculations on a limited scale.

Once the trained data is prepared with regard to each of the characteristic amounts of handwriting data generated by the emotion server apparatus of this embodiment, the trained data may be stored, for example, in the tablet terminal or in the personal computer that processes the handwriting data from the tablet terminal. This allows the tablet terminal or the personal computer to estimate the emotional state from the handwriting data using the trained data stored therein.

In the above example of AI, it is obviously possible to generate the trained data about each electronic pen user by associating the pen state information with each pen ID, or to generate the trained data not for use with regard to individual users but for general use.

DESCRIPTION OF REFERENCE SYMBOLS

1, 1A, 1B . . . Electronic pen, 2, 2A, 2B, 2D . . . Tablet terminal, 4 . . . Association processing device, 5 . . . Electroencephalograph, 5A . . . Simple electroencephalograph, 5B . . . Biological information detection apparatus, 7, 7D . . . Communication network, 8, 8D . . . Emotion server apparatus, 87 . . . Emotion estimation-oriented database, 88 . . . Emotional state estimation request reception circuit, 89 . . . Emotional state estimation circuit, 90 . . . Providing information generation circuit, 234 . . . Emotional state estimation request generation circuit

The invention claimed is:

1. A coordinate input processing apparatus comprising:
   a position detection apparatus that includes a sensor which, in operation, detects a position pointed to by an electronic pen, and circuitry which, in operation, acquires pen state information regarding a state of the electronic pen held by a person; and
   a communication circuit which, in operation, transmits to an emotion estimation apparatus coordinates corresponding to the position pointed to by the electronic pen and the pen state information in an emotional state estimation request having a format that includes a plurality of fields configured to respectively store the coordinates corresponding to the position pointed to by the electronic pen, the pen state information, and information regarding an emotional state of the person holding the electronic pen, and receives from the emotion estimation apparatus the coordinates corresponding to the position pointed to by the electronic pen, the pen state information included in the emotional state estimation request, and the information regarding the emotional state of the person holding the electronic pen in an emotional state estimation response having the format that includes the plurality of fields configured to respectively store the coordinates corresponding to the position pointed to by the electronic pen, the pen state information, and the information regarding the emotional state of the person holding the electronic pen.

2. The coordinate input processing apparatus according to claim 1, wherein:
   the position detection apparatus acquires identification information regarding the electronic pen from the electronic pen,
   the communication circuit, in operation, transmits to the emotion estimation apparatus the coordinates corresponding to the position pointed to by the electronic pen, the pen state information, and the identification information regarding the electronic pen,
   the plurality of fields of the emotion estimation request is configured to respectively store the coordinates corresponding to the position pointed to by the electronic pen, the pen state information, the identification information regarding the electronic pen, and the information regarding the emotional state of the person holding the electronic pen, and
   the plurality of fields of the emotion estimation response is configured to respectively store the coordinates corresponding to the position pointed to by the electronic pen, the pen state information, the identification information regarding the electronic pen, and the information regarding the emotional state of the person holding the electronic pen.

3. The coordinate input processing apparatus according to claim 1, further comprising:
   a storage device which, in operation, stores identification information regarding the coordinate input processing apparatus, wherein:
   the communication circuit, in operation, transmits to the emotion estimation apparatus the coordinates corresponding to the position pointed to by the electronic pen, the pen state information acquired by the position detection apparatus, and the identification information regarding the coordinate input processing apparatus read from the storage device.

4. The coordinate input processing apparatus according to claim 1,
   wherein the coordinate input processing apparatus further comprises:
   a display device that includes a display screen; and
   a processor which, in operation, causes the information regarding to the emotional state received from the emotion estimation apparatus to be reflected in an image on the display screen.

5. The coordinate input processing apparatus according to claim 1, wherein the pen state information includes information regarding a writing pressure applied to the electronic pen, a tilt of the electronic pen relative to a pointing input surface, a height of the electronic pen from the pointing input surface, a movement of the electronic pen detected on the pointing input surface, and a movement speed of pointing input with the electronic pen.

6. The coordinate input processing apparatus according to claim 1, wherein
the position detection apparatus and the communication circuit are included in an information processing apparatus.

7. The coordinate input processing apparatus according to claim 1, wherein
the position detection apparatus and an information processing apparatus including the communication circuit are separate and are connected with one another in a wired or a wireless fashion.

8. An emotion estimation apparatus comprising:
a communication circuit which, in operation, receives coordinates corresponding to a position pointed to by an electronic pen and pen state information acquired by a position detection apparatus in an emotional state estimation request having a format that includes a plurality of fields configured to respectively store the coordinates corresponding to the position pointed to by the electronic pen, the pen state information, and information regarding an emotional state of the person holding the electronic pen;
an emotion estimation-oriented information storage device which, in operation, stores information regarding the emotional state of the person holding the electronic pen and range information regarding a range of values that may be taken by the coordinates corresponding to the position pointed to by the electronic pen and the pen state information regarding a state of the electronic pen held by the person at a time of being in the emotional state, the information regarding the emotional state and the range information being associated with one another; and
a processor which, upon receipt of the emotional state estimation request from a coordinate input processing apparatus, estimates the emotional state of the person holding the electronic pen having transmitted the emotional state estimation request by referencing the emotion estimation-oriented information storage device, and generates an emotional state estimation response including the information regarding the estimated emotional state of the person holding the electronic pen, the emotional state estimation response having the format that includes the plurality of fields configured to respectively store the coordinates corresponding to the position pointed to by the electronic pen, the pen state information, and the information regarding the emotional state of the person holding the electronic pen.

9. The emotion estimation apparatus according to claim 8, wherein the processor, in operation, notifies a party that transmitted the emotional state estimation request of the estimated emotional state.

10. The emotion estimation apparatus according to claim 8, wherein:
the emotion estimation-oriented information storage device stores the information regarding the emotional state and the range information regarding the range of values that may be taken by the coordinates corresponding to the position pointed to by the electronic pen, the pen state information regarding the state of the electronic pen held by the person performing pointing input at the time of being in the emotional state, the information regarding the emotional state and the range information being associated with identification information identifying the person manifesting the emotional state, wherein the range information that may be taken by the coordinates corresponding to the position pointed to by the electronic pen include a first range of coordinates corresponding to the position pointed to by the electronic pen while the sensor is in contact with the electronic pen and a second range of coordinates corresponding to the position pointed to by the electronic pen while the sensor is not in contact with the electronic pen; and
upon receipt of the emotional state estimation request including the pen state information regarding the state of the electronic pen and the identification information identifying the person manifesting the emotional state, the processor references the information stored in the emotion estimation-oriented information storage device in association with the identification information identifying the person manifesting the emotional state.

11. The emotion estimation apparatus according to claim 10, wherein
the identification information identifies the electronic pen held by the person.

12. The emotion estimation apparatus according to claim 10, wherein
the identification information identifies an electronic device including a position detection apparatus that detects pointing input performed with the electronic pen held by the person.

13. The emotion estimation apparatus according to claim 9, wherein:
the pen state information includes writing pressure data, tilt data, height position data, time data, and pen identification data, and
the plurality of fields is configured to respectively store the coordinates corresponding to the position pointed to by the electronic pen, the writing pressure data, the tilt data, the height position data, the time data, and the pen identification data.

14. An emotion estimation system comprising:
a coordinate input processing apparatus; and
an emotion estimation apparatus connected with the coordinate input processing apparatus via a communication network,
wherein the coordinate input processing apparatus includes:
an electronic pen;
a position detection apparatus that includes a sensor which, in operation, detects a position pointed to by the electronic pen, and circuitry, which in operation, acquires pen state information regarding a state of the electronic pen held by a person; and
a communication circuit which, in operation, receives coordinates corresponding to the position pointed to by the electronic pen and the pen state information, and transmits to the emotion estimation apparatus coordinates corresponding to the position pointed to by the electronic pen and the pen state information in an emotional state estimation request having a format that includes a plurality of fields configured to respectively store the coordinates corresponding to the position pointed to by the electronic pen, the pen state information, and information regarding an emotional state of the person holding the electronic pen; and wherein the emotion estimation apparatus includes:
a receiver which, in operation, receives the coordinates corresponding to the position pointed to by the electronic pen and the pen state information in the format that includes the plurality of fields configured to respectively store the coordinates corresponding to the position pointed to by the electronic pen, the pen state information acquired by the position detection apparatus, and the information regarding the emotional state of the person holding the electronic pen;
an emotion estimation-oriented information storage device which, in operation, stores information regarding to an emotional state of the person holding the electronic pen and range information regarding a range of values that may be taken by the coordinates corresponding to the position pointed to by the electronic pen and the pen state information regarding the state of the electronic pen held by the person at the time of being in the emotional state, the information regarding to the emotional state and the range information being associated with one another; and
a processor which, in operation, upon receipt of an emotional state estimation request, estimates the emotional state of a person holding the electronic pen having transmitted the emotional state estimation request by referencing the emotion estimation-oriented information storage device, and generates an emotional state estimation response including the coordinates corresponding to the position pointed to by the electronic pen, the pen state information acquired by the position detection apparatus, and the information corresponding to the estimated emotional state, in the format that includes the plurality of fields configured to respectively store the coordinates corresponding to the position pointed to by the electronic pen, the pen state information acquired by the position detection apparatus, and the information regarding the emotional state of the person holding the electronic pen.

15. The emotion estimation system according to claim 14, wherein:
the pen state information includes writing pressure data, tilt data, height position data, time data, and pen identification data, and
the plurality of fields is configured to store the coordinates corresponding to the position pointed to by the electronic pen, the writing pressure data, the tilt data, the height position data, the time data, and the pen identification data.

16. A building apparatus that builds an emotion estimation-oriented information storage device, the building apparatus comprising:
at least one processor; and
at least one storage device storing processor-readable instructions that, when executed by the at least one processor, cause the building apparatus to:
acquire biological information regarding a person performing pointing input using an electronic pen;
acquire pen state information regarding the state of the electronic pen held by the person performing the pointing input and associated with the acquired biological information;
discriminate an emotional state of the person holding the electronic pen based on the biological information;
obtain range information regarding a range of values that may be taken by the coordinates corresponding to the position pointed to by the electronic pen and the pen state information at a time of the emotional state from the acquired pen state information, wherein the range information includes a first range of coordinates corresponding to a plurality of positions pointed to by the electronic pen while a sensor is in contact with the electronic pen and a second range of coordinates corresponding to a plurality of positions pointed to by the electronic pen while the sensor is not in contact with the electronic pen;
store information regarding the emotional state and the range information regarding the range of values that may be taken by the coordinates corresponding to the position pointed to by the electronic pen and the pen state information into the emotion estimation-oriented information storage device, the information regarding the emotional state and the range information being associated with one another;
receive an emotional state estimation request; and
generate an emotional state estimation response including the information regarding the emotional state.

17. The building apparatus that builds the emotion estimation-oriented information storage device according to claim 16, wherein the processor-readable instructions, when executed by the at least one processor, cause the building apparatus to:
acquire identification information identifying the person manifesting the emotional state in association with the pen state information; and
store the information regarding the emotional state, the range information regarding the range in which the pen state information is present, and identification information identifying the electronic pen into the emotion estimation-oriented information storage device, the information regarding the emotional state being associated with the range information and the identification information.

18. The building apparatus that builds the emotion estimation-oriented information storage device according to claim 17, wherein
the identification information is identification information regarding the electronic pen held by the person.

19. The building apparatus that builds the emotion estimation-oriented information storage device according to claim 17, wherein
the identification information is identification information regarding an electronic device including the position detection apparatus that detects pointing input performed with the electronic pen held by the person.

20. The building apparatus that builds the emotion estimation-oriented information storage according to claim 19, wherein the instructions, when executed by the at least one processor, cause the building apparatus to:
obtain range information regarding a range of values corresponding to a height of the electronic pen above a sensor surface; and
store information regarding the range of values corresponding to the height of the electronic pen above the sensor surface, information regarding the range of values corresponding to the height of the electronic pen above the sensor surface being associated with the information regarding the emotional state and the range information.

21. The building apparatus for building the emotion estimation-oriented information storage device according to claim 16, wherein:
the electronic pen includes a receiver which, in operation, receives the biological information by wireless communication, the electronic pen further supplying the position detection apparatus with the biological information received by the receiver,
the electronic pen includes the biological information in information added to a position detection signal transmitted by the electronic pen; and
the processor-readable instructions, when executed by the at least one processor, cause the building apparatus to acquire the biological information and the pen state information from the position detection signal transmitted by the position detection apparatus.

22. An emotion estimation system comprising:
a coordinate input processing apparatus including an electronic pen, a sensor which, in operation, detects a position pointed by the electronic pen, circuitry which, in operation, acquires pen state information regarding the electronic pen held by a person, and a communication circuit which, in operation, transmits coordinates corresponding to the position pointed to by the electronic pen and the pen state information in an emotional state estimation request having a format that includes a plurality of fields configured to respectively store the coordinates corresponding to the position pointed to by the electronic pen, the pen state information, and information regarding an emotional state the person holding the electronic pen; and
an emotion estimation apparatus including at least one processor, and at least one storage device storing processor-readable instructions that, when executed by the at least one processor, cause the emotion estimation apparatus to acquire the coordinates corresponding to the position pointed to by the electronic pen and pen state information from the emotional state estimation request transmitted by the coordinate input processing apparatus and to acquire biological information, and an emotion estimation-oriented information storage device which, in operation, stores information regarding an emotional state of the person holding the electronic pen and range information regarding a range of values that may be taken by the coordinates corresponding to the position pointed to by the electronic pen and the pen state information, the information regarding the emotional state and the range information being associated with one another;
wherein the communication circuit of the coordinate input processing apparatus, in operation:
receives information that identifies either the biological information or the emotional state discriminated from the biological information; and
transmits to the emotion estimation apparatus an emotional state estimation request including the coordinates corresponding to the position pointed to by the electronic pen and the pen state information acquired by the coordinate input processing apparatus; and
wherein the at least one storage device stores processor-readable instructions, when executed by the at least one processor, causes the emotion estimation apparatus to:
upon receipt of a data building request from the coordinate input processing apparatus, store into the emotion estimation-oriented information storage device the information regarding the emotional state of the person holding the electronic pen and the range information regarding the range of values that may be taken by the pen state information regarding the state of the electronic pen held by the person at the time of being in the emotional state, the information regarding the emotional state and the range information being associated with one another; and
upon receipt of the emotion estimation request from the coordinate input processing apparatus, estimate the emotional state of the person holding the electronic pen having transmitted the emotional state estimation request by referencing the emotion estimation-oriented information storage device by use of the received pen state information, generates an emotional state estimation response including the coordinates corresponding to the position pointed to by the electronic pen, the pen state information, and information corresponding to the emotional state, and return the generated information to the coordinate input processing apparatus having made the emotional state estimation request, the emotional state estimation response having the format that includes the plurality of fields configured to respectively store the coordinates corresponding to the position pointed to by the electronic pen, the pen state information, and the information regarding the emotional state of the person holding the electronic pen.

23. The emotion estimation system according to claim 22, wherein:
the pen state information includes coordinate data, writing pressure data, tilt data, height position data, time data, and pen identification data, and
the plurality of fields is configured to respectively store the coordinate data, the writing pressure data, the tilt data, the height position data, the time data, the pen identification data, and the biological information.

24. An emotion estimation apparatus comprising:
a communication circuit which, in operation, receives coordinates corresponding to a position pointed to by an electronic pen and pen state information acquired by a position detection apparatus in an emotional state estimation request having a format that includes a plurality of fields configured to respectively store the coordinates corresponding to a position pointed to by the electronic pen and the pen state information, information regarding an emotional state of the person holding the electronic pen;
at least one processor; and
at least one storage device storing processor-readable instructions that, when executed by the at least one processor, cause the emotion estimation apparatus to:
store information regarding an emotional state of a person holding the electronic pen and pen state information regarding the state of the electronic pen held by the person at a time of being in the emotional state, the information regarding the emotional state and the pen state information being associated with one another;
generate trained data by performing machine learning using the pen state information acquired by the position detection apparatus and biological information detected by a biological information detection apparatus worn by the person holding the electronic pen;

upon receipt of an emotional state estimation request including the pen state information regarding the electronic pen, using the trained data to estimate the emotional state of the person holding the electronic pen having transmitted the request information based on the received pen state information; and generate an emotional state estimation response including the coordinates corresponding to the position pointed to by the electronic pen, the pen state information, and the information regarding the emotional state of the person holding the electronic pen, the emotional state estimation response having the format that includes the plurality of fields configured to respectively store the coordinates corresponding to the position pointed to by the electronic pen, the pen state information, and the information regarding the emotional state of the person holding the electronic pen.

25. The emotion estimation apparatus according to claim 24, wherein the pen state information comprises a plurality of characteristic amounts; and the trained data is generated for each of the plurality of characteristic amounts in the pen state information.

26. The emotion estimation apparatus according to claim 24, wherein the pen state information includes coordinate data, writing pressure data, tilt data, height position data, time data, and pen identification data, and the plurality of fields is configured to store coordinate data, the writing pressure data, the tilt data, the height position data, the time data, the pen identification data, and the biological information.

* * * * *